(12) United States Patent
Folan et al.

(10) Patent No.: US 10,687,969 B2
(45) Date of Patent: Jun. 23, 2020

(54) STENT DELIVERY SYSTEM

(71) Applicant: BOSTON SCIENTIFIC SCIMED, INC., Maple Grove, MN (US)

(72) Inventors: Martyn G. Folan, Loughrea (IE);
Gerasimos Rigalos, Galway (IE);
Thomas M. Keating, Galway (IE);
Michael Gerard Walsh, Galway (IE);
Bryan M. Forde, Galway (IE)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 211 days.

(21) Appl. No.: 15/635,872

(22) Filed: Jun. 28, 2017

(65) Prior Publication Data
US 2018/0000620 A1   Jan. 4, 2018

Related U.S. Application Data

(60) Provisional application No. 62/356,143, filed on Jun. 29, 2016.

(51) Int. Cl.
*A61F 2/966* (2013.01)
*A61F 2/97* (2013.01)
(Continued)

(52) U.S. Cl.
CPC .............. *A61F 2/966* (2013.01); *A61B 90/08* (2016.02); *A61F 2/82* (2013.01); *A61F 2/852* (2013.01);
(Continued)

(58) Field of Classification Search
CPC ............. A61B 2090/0811; A61B 90/08; A61F 2002/826; A61F 2002/9517;
(Continued)

(56) References Cited

U.S. PATENT DOCUMENTS

| 5,078,720 A | 1/1992 | Burton et al. |
| 5,201,757 A | 4/1993 | Heyn et al. |

(Continued)

FOREIGN PATENT DOCUMENTS

| EP | 2777653 A1 | 9/2014 |
| JP | 2012505002 A | 3/2012 |

(Continued)

OTHER PUBLICATIONS

International Search Report and Written Opinion dated Sep. 26, 2017 for International Application No. PCT/US2017/039718.

*Primary Examiner* — Ryan J. Severson
*Assistant Examiner* — Mohamed G Gabr
(74) *Attorney, Agent, or Firm* — Seager, Tufte & Wickhem, LLP

(57) ABSTRACT

Stent delivery device including an inner member having a distal tip, a stent support member, and a stent disposed over a stent receiving region of the stent support member. An elongated outer sheath is slidably disposed over the inner member and the stent. The stent delivery device includes a distal junction removably coupling the distal end of the outer sheath to the distal tip, where the distal junction is actuatable to decouple the outer sheath from the distal tip. The stent delivery device includes a proximal junction removably coupling a distal portion of the outer sheath to a proximal portion of the outer sheath, where the proximal junction is actuatable to decouple the distal portion of the outer sheath from the proximal portion of the outer sheath. The distal and proximal junctions may be separately actuatable by rotating the inner member relative to the proximal portion of the outer sheath.

16 Claims, 16 Drawing Sheets

(51) Int. Cl.
- *A61F 2/852* (2013.01)
- *A61F 2/95* (2013.01)
- *A61B 90/00* (2016.01)
- *A61F 2/82* (2013.01)

(52) U.S. Cl.
CPC ......... *A61F 2/97* (2013.01); *A61B 2090/0811* (2016.02); *A61F 2002/826* (2013.01); *A61F 2002/9517* (2013.01); *A61F 2002/9665* (2013.01); *A61F 2220/0033* (2013.01); *A61F 2220/0041* (2013.01); *A61F 2250/0097* (2013.01)

(58) Field of Classification Search
CPC ...... A61F 2002/9665; A61F 2220/0033; A61F 2220/0041; A61F 2250/0097; A61F 2/82; A61F 2/852; A61F 2/966; A61F 2/97
See application file for complete search history.

(56) References Cited

U.S. PATENT DOCUMENTS

| | | | |
|---|---|---|---|
| 5,242,399 A | 9/1993 | Lau et al. | |
| 5,275,622 A | 1/1994 | Lazarus et al. | |
| 5,415,664 A | 5/1995 | Pinchuk | |
| 5,445,646 A | 8/1995 | Euteneuer et al. | |
| 5,534,007 A * | 7/1996 | St. Germain | A61F 2/95 606/191 |
| 5,603,698 A | 2/1997 | Roberts et al. | |
| 5,902,333 A | 5/1999 | Roberts et al. | |
| 5,980,533 A | 11/1999 | Holman | |
| 6,241,758 B1 | 6/2001 | Cox | |
| 6,582,460 B1 | 6/2003 | Cryer | |
| 6,849,084 B2 | 2/2005 | Rabkin et al. | |
| 6,994,721 B2 | 2/2006 | Israel | |
| 7,004,964 B2 | 2/2006 | Thompson et al. | |
| 7,074,236 B2 | 6/2006 | Rabkin et al. | |
| 7,235,095 B2 | 6/2007 | Haverkost et al. | |
| 7,331,985 B2 | 2/2008 | Thompson et al. | |
| 7,887,573 B2 | 2/2011 | Haverkost et al. | |
| 8,048,148 B2 | 11/2011 | Viller | |
| 8,518,098 B2 | 8/2013 | Roeder et al. | |
| 8,747,459 B2 | 6/2014 | Nguyen et al. | |
| 8,864,811 B2 | 10/2014 | Kao | |
| 9,101,507 B2 | 8/2015 | Caselnova | |
| 9,295,550 B2 | 3/2016 | Nguyen et al. | |
| 9,301,864 B2 | 4/2016 | Kao | |
| 9,314,360 B2 | 4/2016 | Kao | |
| 2003/0163189 A1 | 8/2003 | Thompson et al. | |
| 2004/0127912 A1 | 7/2004 | Rabkin et al. | |
| 2005/0288764 A1 | 12/2005 | Snow et al. | |
| 2006/0136036 A1 | 6/2006 | Thompson et al. | |
| 2006/0142837 A1 | 6/2006 | Haverkost et al. | |
| 2007/0156225 A1 * | 7/2007 | George | A61F 2/95 623/1.12 |
| 2007/0233222 A1 | 10/2007 | Roeder et al. | |
| 2008/0294230 A1 | 11/2008 | Parker | |
| 2009/0264978 A1 | 10/2009 | Dieck et al. | |
| 2011/0307049 A1 * | 12/2011 | Kao | A61F 2/966 623/1.11 |

FOREIGN PATENT DOCUMENTS

| | | |
|---|---|---|
| WO | 9526775 A1 | 10/1995 |
| WO | 03051425 A2 | 6/2003 |
| WO | 2006133960 A1 | 12/2006 |

* cited by examiner

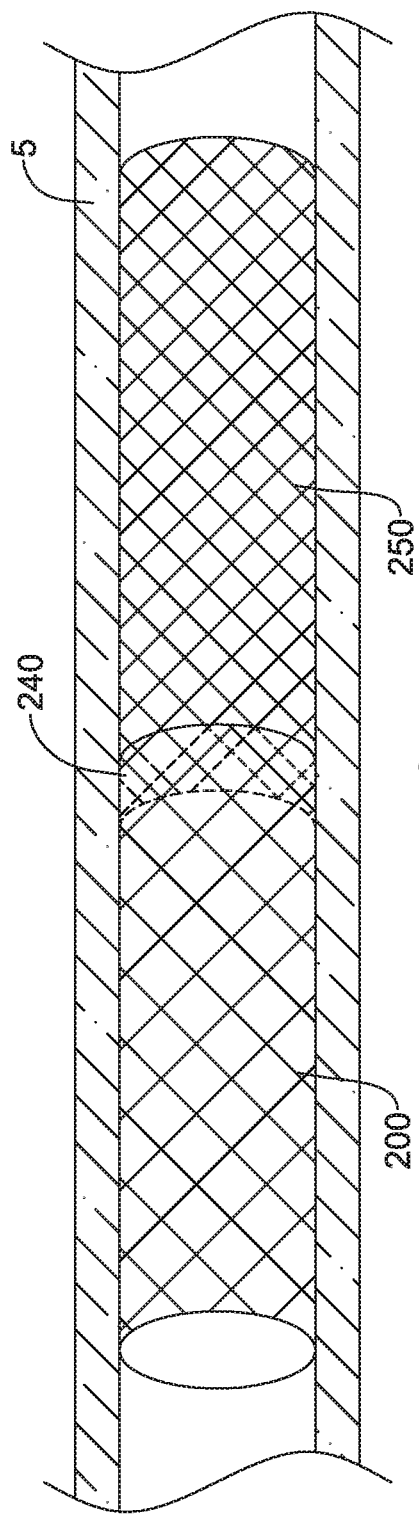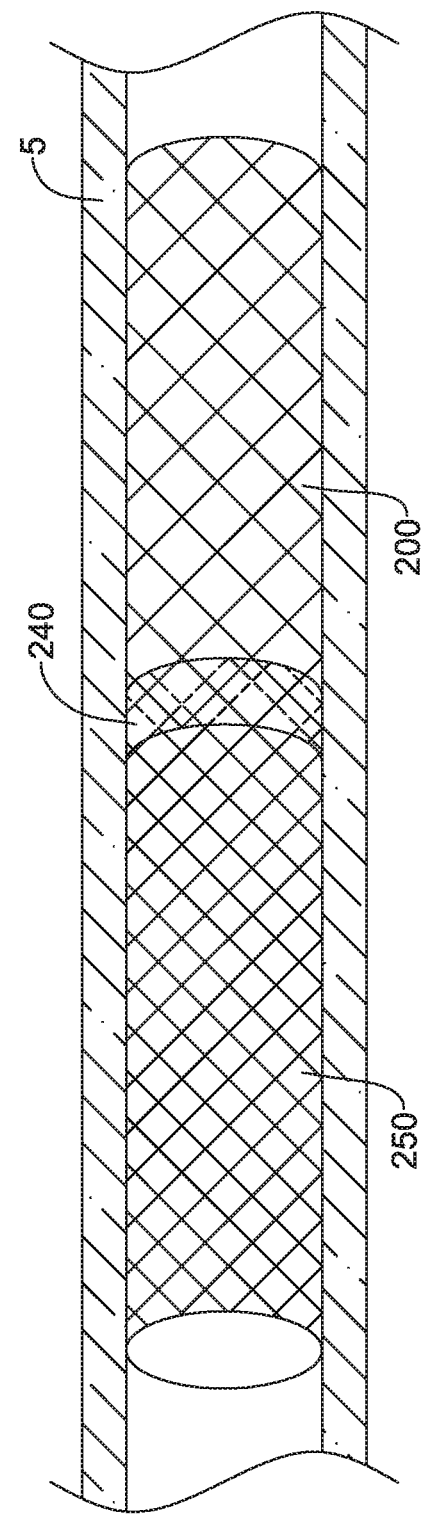

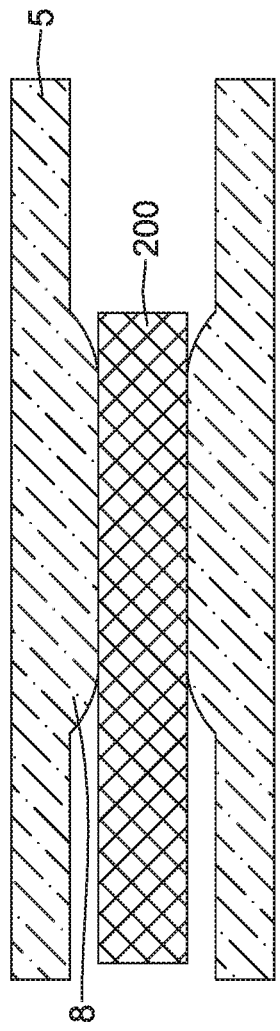
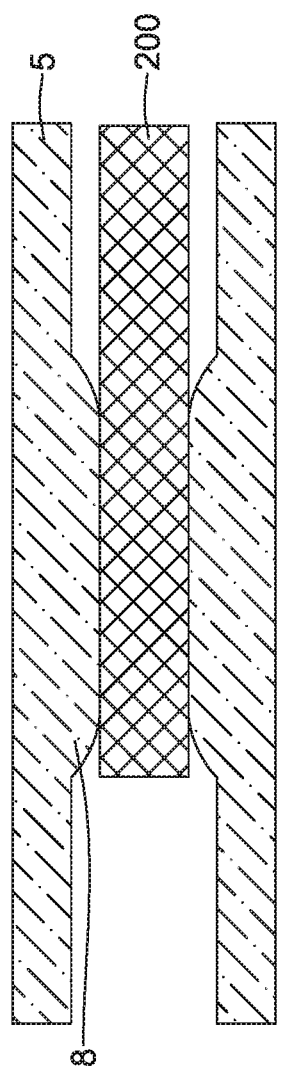
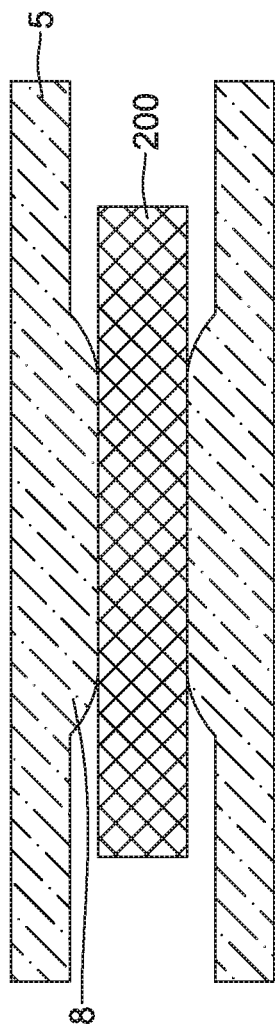

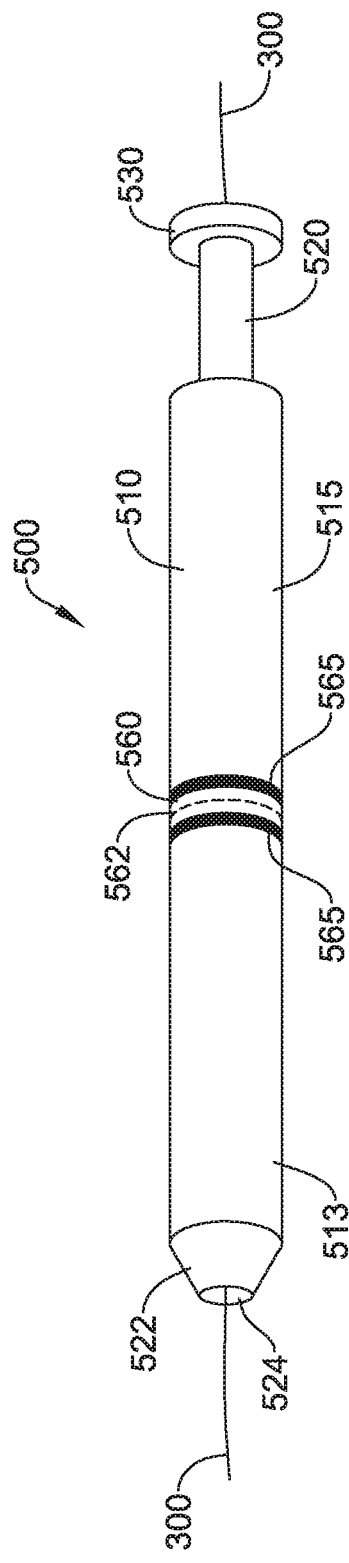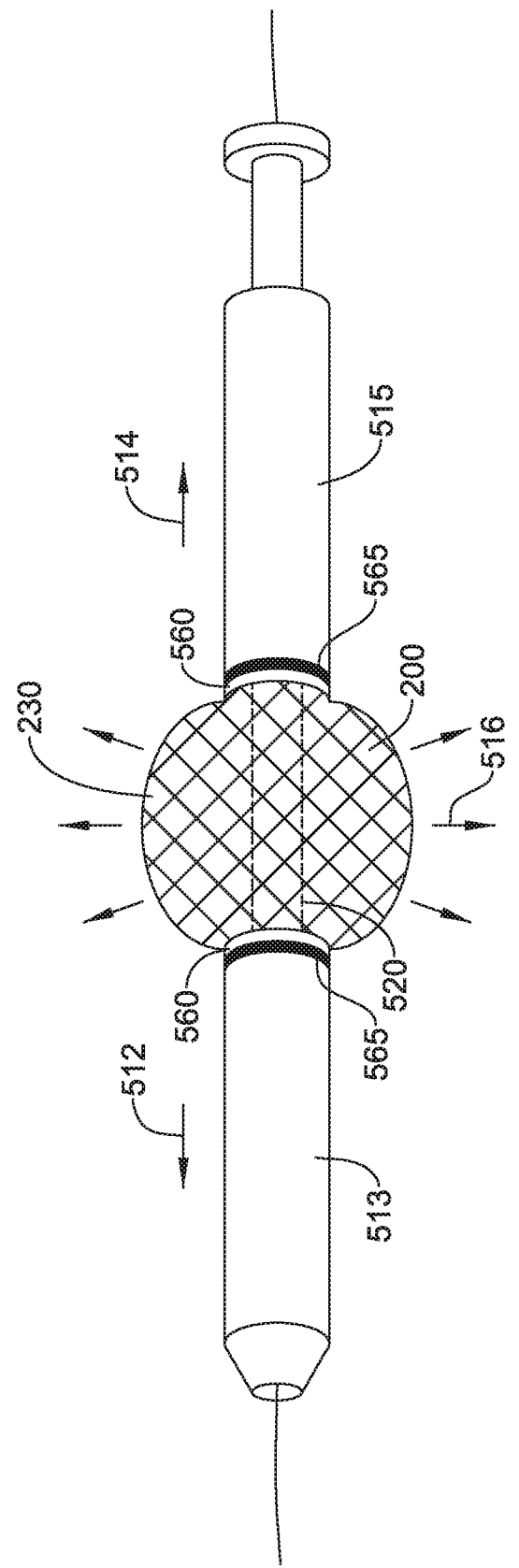

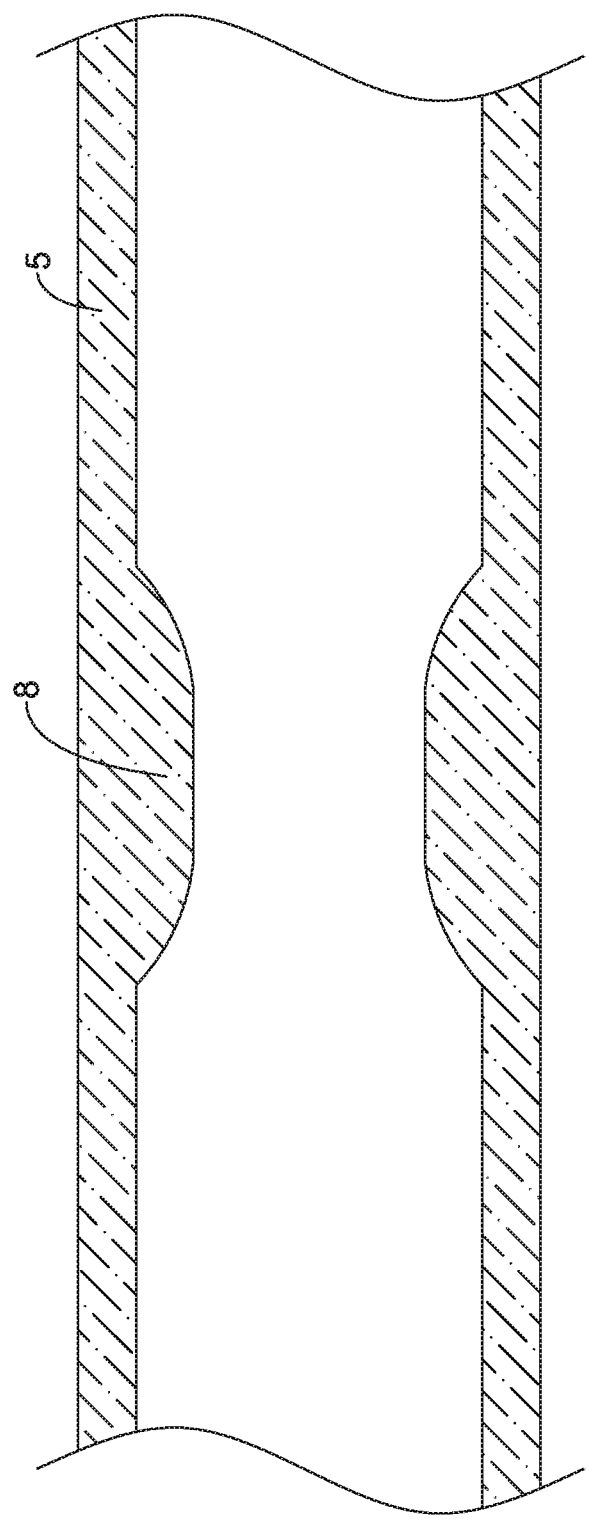

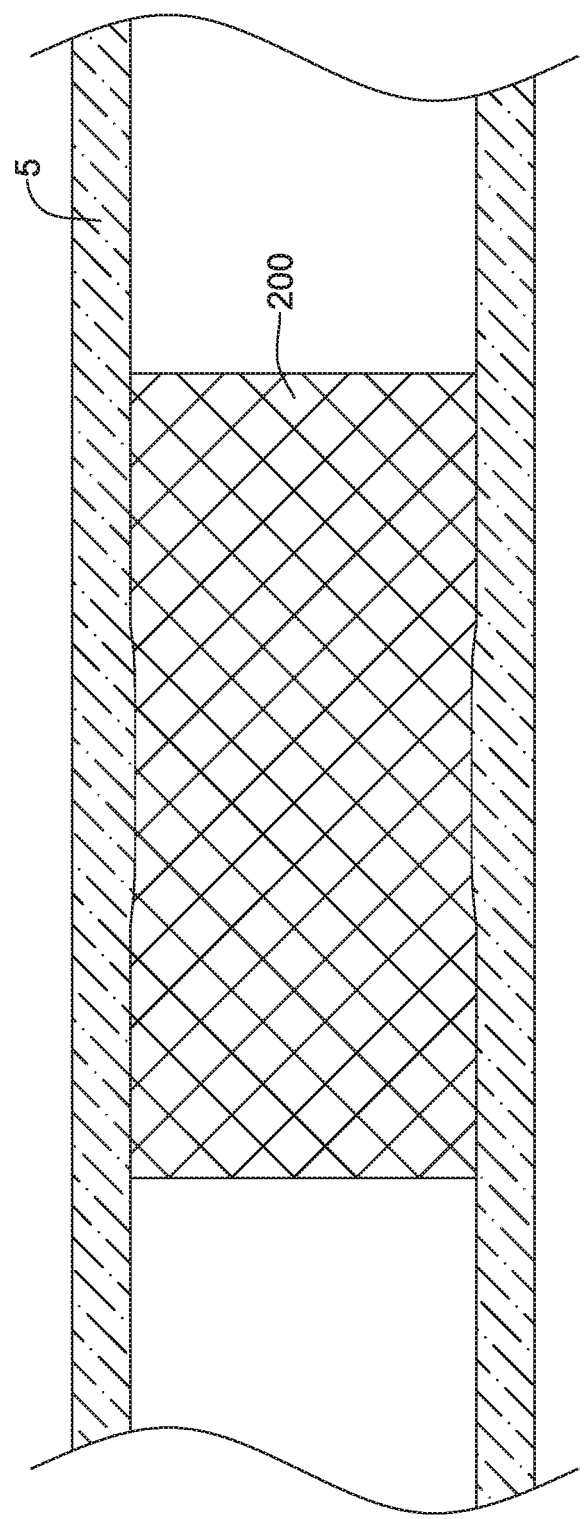

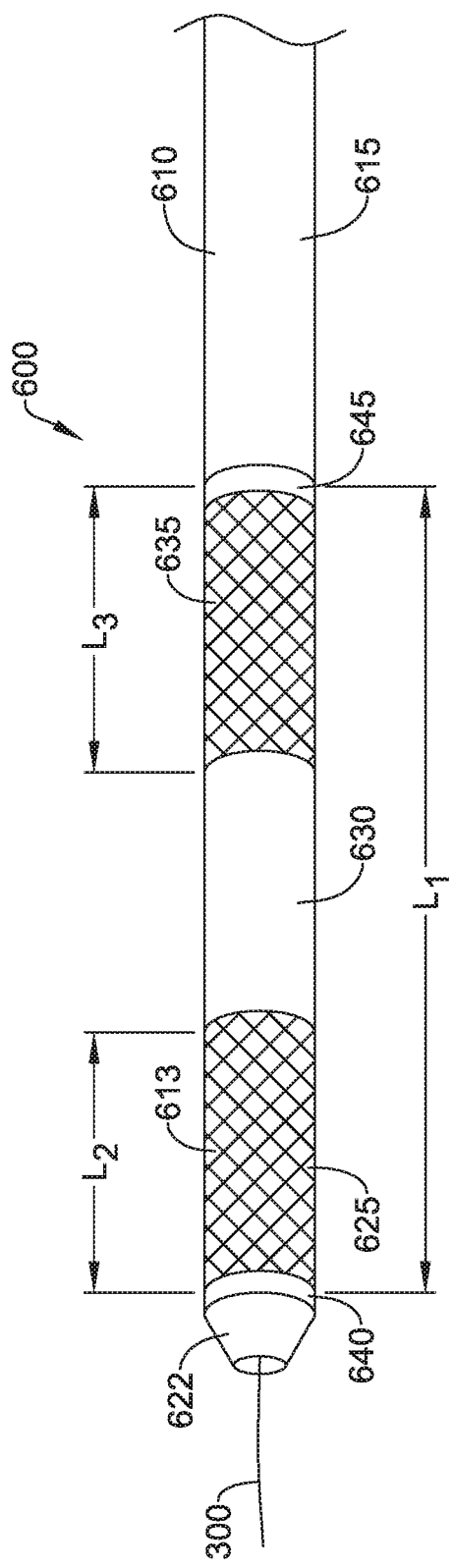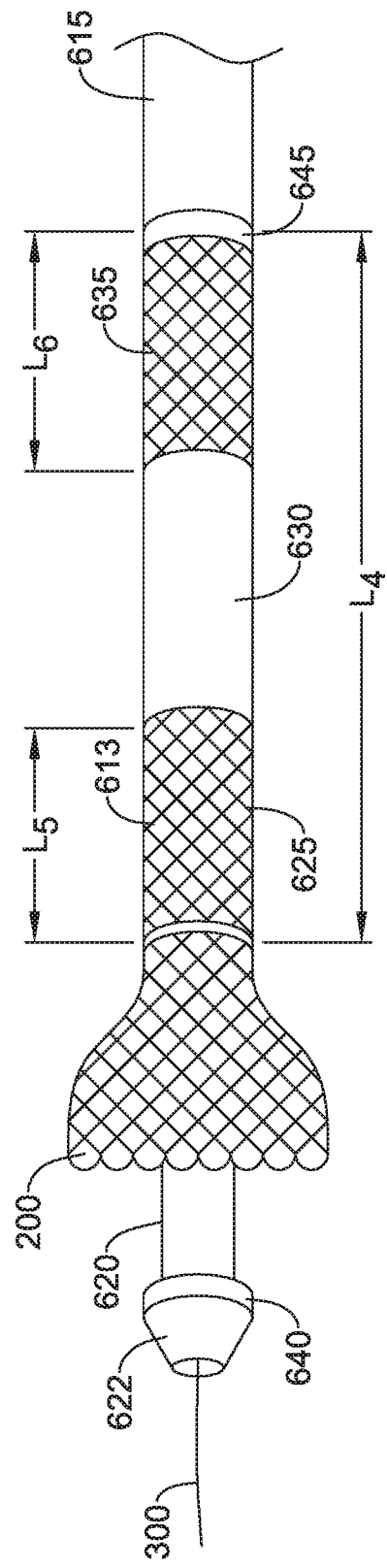

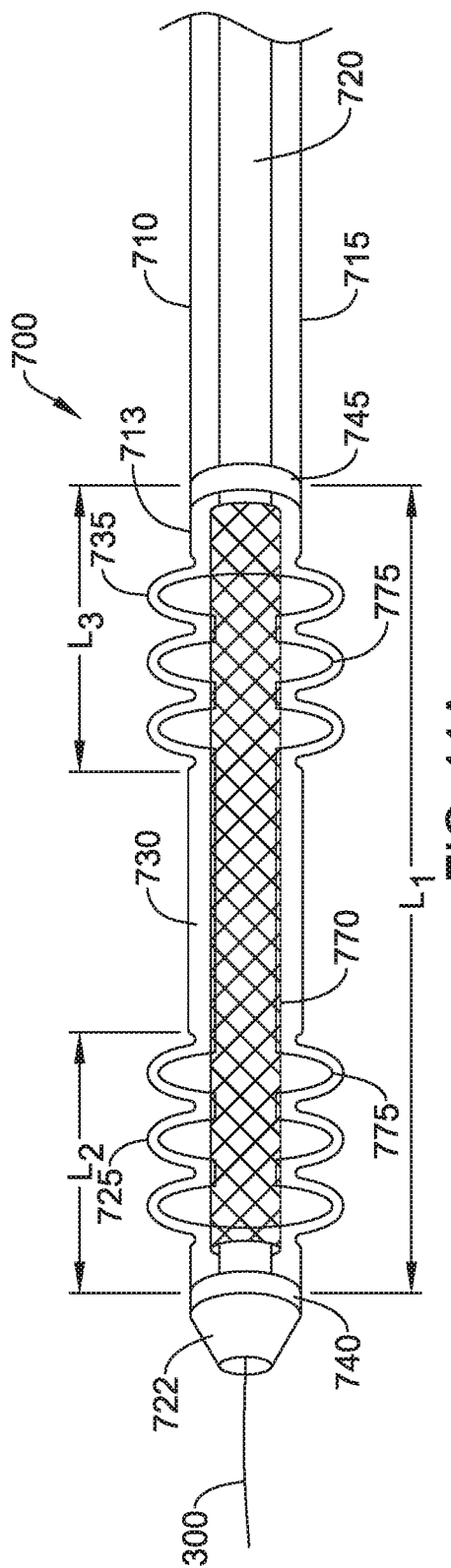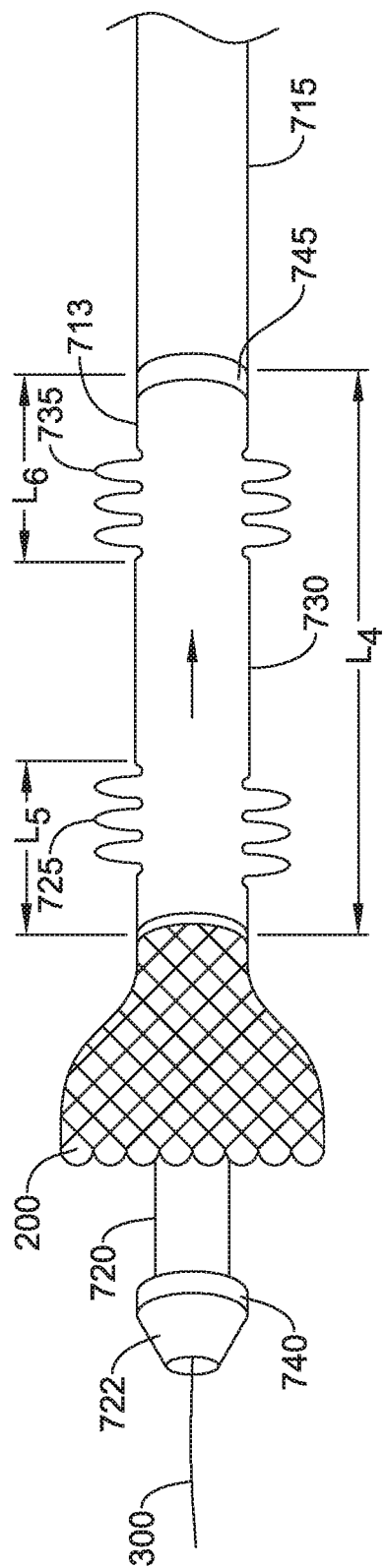
FIG. 11A
FIG. 11B

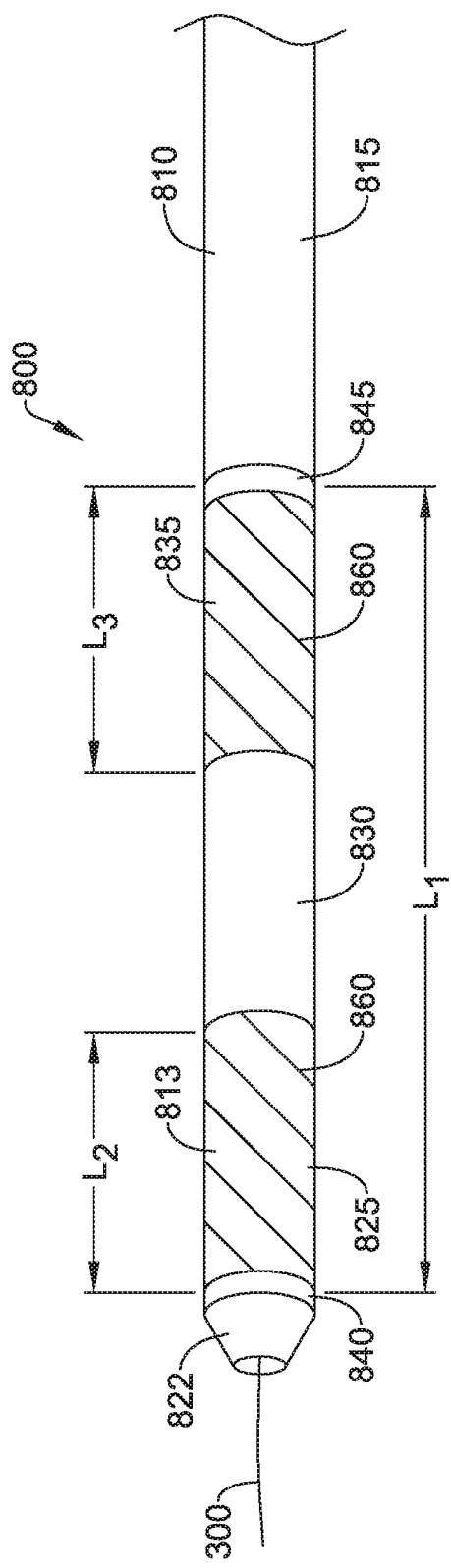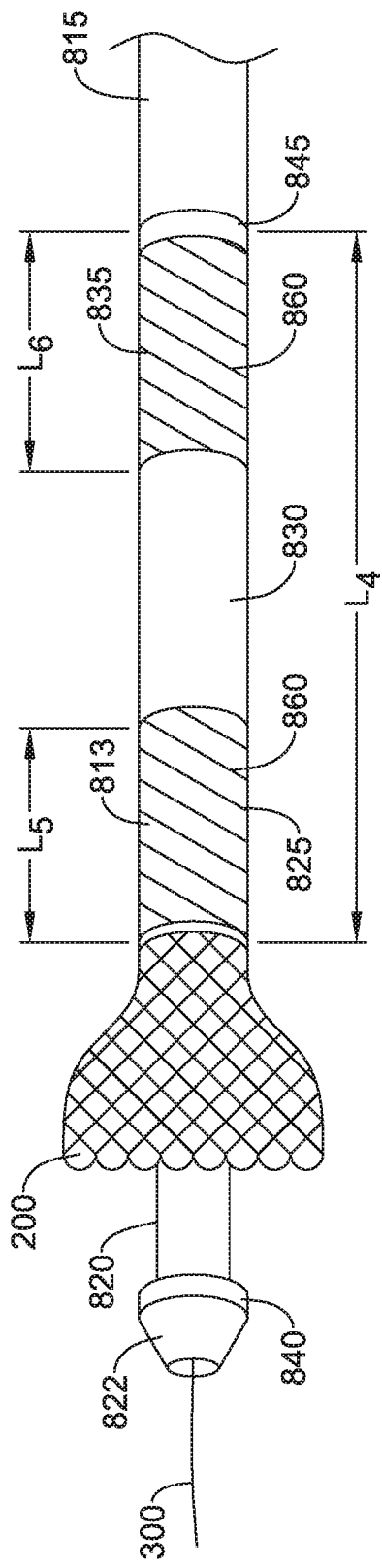

STENT DELIVERY SYSTEM

CROSS REFERENCE TO RELATED APPLICATIONS

This application claims the benefit of U.S. Provisional Patent Application Ser. No. 62/356,143 filed on Jun. 29, 2016, the disclosure of which is incorporated herein by reference.

TECHNICAL FIELD

The disclosure is directed to devices for delivering self-expanding stents. More particularly, the disclosure is directed to a device that selectively deploys a stent in a distal to proximal or a proximal to distal manner.

BACKGROUND

Delivery devices for self-expanding stents, such as those used in endoscopic applications, generally have an outer sheath that retracts to allow the stent to expand radially at the target site. Retraction of the outer sheath in the proximal direction exposes the stent in a distal to proximal direction, thus allows the distal end of the stent to expand first, providing a distal-to-proximal direction of expansion. This manner of deployment may allow the distal end of the stent to be placed in a particular location. However, the final location of the proximal end of the stent may not be known until the stent is fully expanded due to the self-expanding stent characteristics. When a specific location of the proximal end of the stent is desired, deploying the stent in a distal-to-proximal manner may require estimation of where the proximal end will reside upon complete expansion of the stent. Such an estimation may not have the desired precision needed for proper placement of the stent. There is an ongoing need to provide alternative delivery devices to selectively deploy stents in either a distal-to-proximal or proximal-to-distal manner.

BRIEF SUMMARY

This disclosure provides design, material, and use alternatives for medical devices, including delivery systems.

In a first example, a stent delivery system includes an elongated inner member extending between a distal tip and a proximal end. A stent support member is disposed over or surrounding the inner member includes a stent receiving region proximal of the distal tip. The inner member is slidable within the stent support member. The system also includes at least one stent surrounding the stent receiving region of the stent support member. The stent has a collapsed configuration and an expanded configuration. The system further includes an elongated outer sheath slidably disposed over the inner member. The outer sheath extends between a distal end and a proximal end, and includes a proximal portion and a distal portion located distal of the proximal portion. The distal portion of the outer sheath surrounds the stent to restrain the stent in the collapsed configuration. A proximal junction detachably couples the distal portion of the outer sheath to the proximal portion of the outer sheath. The proximal junction is actuatable to selectively uncouple the distal portion of the outer sheath from the proximal portion of the outer sheath. A distal junction detachably couples the distal end of the outer sheath to the distal tip of the inner member. The distal junction is actuatable to selectively uncouple the outer sheath from the distal tip. The distal and proximal junctions are separately actuatable by rotating the inner member relative to the proximal portion of the outer sheath.

Alternatively or additionally, in another example, the distal junction includes a first distal junction element disposed on the distal tip and a second distal junction element disposed on the distal end of the outer sheath, wherein the first and second distal junction elements are rotatably coupled to each other.

Alternatively or additionally, in another example, the proximal junction includes a first proximal junction element disposed on a proximal end of the distal portion of the outer sheath, a second proximal junction element disposed on a distal end of the proximal portion of the outer sheath, wherein the first and second proximal junction elements are rotatably coupled to each other.

Alternatively or additionally, in another example, the stent is deployable from a proximal-to-distal manner by uncoupling the proximal junction and moving the distal portion of the outer sleeve distally relative to the stent.

Alternatively or additionally, in another example, the stent is deployable from a distal-to-proximal manner by uncoupling the distal junction and moving the distal portion of the outer sleeve proximally relative to the stent.

Alternatively or additionally, in another example, the system further includes a handle assembly at the proximal end of the inner member, wherein the handle assembly includes a position marker and first and second spaced apart rotational markers indicating a rotational orientation of the inner member.

Alternatively or additionally, in another example, the proximal junction is uncoupled when the position marker is aligned with the first rotational marker, and wherein the distal junction is uncoupled when the position marker is aligned with the second rotational marker.

Alternatively or additionally, in another example, the handle assembly includes a start position marker located between the first rotational marker and the second rotational marker, wherein both the proximal junction and the distal junction are coupled when the position marker is aligned with the start position marker.

Alternatively or additionally, in another example, the first and second rotational markers are arranged 180 degrees apart.

Alternatively or additionally, in another example, a length of the distal portion of the outer sheath is at least as long as a length of the stent.

Alternatively or additionally, in another example, the proximal junction is adjacent a proximal end of the stent.

Alternatively or additionally, in another example, the distal and proximal junctions include one or more of a threaded connection, a bayonet connection, a snap fit connection, a keyed connection, a rotational connection, and a barbed connection.

Alternatively or additionally, in another example, the stent is a self-expanding stent.

Alternatively or additionally, in another example, the at least one stent includes a first stent and a second stent, wherein the first and second stents surround the stent receiving region of the stent support member with the first stent positioned distal of the second stent.

Alternatively or additionally, in another example, the distal portion of the outer sheath includes at least one axially collapsible section configured to shorten in axial length when the proximal junction or the distal junction is uncoupled.

Alternatively or additionally, in another example, the at least one axially collapsible section includes a proximal axially collapsible section and a distal axially collapsible section, and the distal portion includes a middle section positioned between the proximal and distal axially collapsible sections, the middle section configured to maintain a constant length when the proximal junction or the distal junction is uncoupled.

In another example, a stent delivery system includes an elongated inner member having a proximal end and a distal end. The inner member includes a distal tip at the distal end. A stent support member is disposed over or surrounds the inner member and has a stent receiving region proximal of the distal tip of the inner member. The inner member is slidably disposed within the stent support member. The system also includes at least one self-expanding stent disposed over the stent receiving region of the stent support member. The stent has a collapsed configuration and an expanded configuration. The system further includes an elongated outer sheath slidably disposed over the inner member. The outer sheath extends between a distal end and a proximal end, and includes a proximal portion and a distal portion located distal of the proximal portion. The distal portion of the outer sheath extends to the distal end of the outer sheath and surrounds the stent to restrain the stent in the collapsed configuration. A proximal junction detachably couples a proximal end of the distal portion of the outer sheath to a distal end of the proximal portion of the outer sheath. The proximal junction is actuatable to selectively uncouple the distal portion of the outer sheath from the proximal portion of the outer sheath by rotating the inner member relative to the proximal portion of the outer sheath in a first rotational direction. A distal junction detachably couples the distal end of the outer sheath to the distal tip of the inner member. The distal junction is actuatable to selectively uncouple the outer sheath from the distal tip by rotating the inner member relative to the proximal portion of the outer sheath in a second rotational direction. The first direction is opposite the second direction.

Alternatively or additionally, in another example, the distal junction includes a first distal junction element disposed on the distal tip and a second distal junction element disposed on the distal end of the outer sheath, wherein the first and second distal junction elements are rotatably coupled to each other.

Alternatively or additionally, in another example, the proximal junction includes a first proximal junction element disposed on the proximal end of the distal portion of the outer sheath, a second proximal junction element disposed on the distal end of the proximal portion of the outer sheath, wherein the first and second proximal junction elements are rotatably coupled to each other.

Alternatively or additionally, in another example, the proximal junction is adjacent a proximal end of the stent.

Alternatively or additionally, in another example, the distal portion of the outer sheath includes at least one axially collapsible section configured to shorten in axial length when the proximal junction or the distal junction is uncoupled.

Alternatively or additionally, in another example, the at least one axially collapsible section includes a proximal axially collapsible section and a distal axially collapsible section, and the distal portion includes a middle section positioned between the proximal and distal axially collapsible sections, the middle section configured to maintain a constant length when the proximal junction or the distal junction is uncoupled.

In another example, a method of selectively deploying a stent in a proximal-to-distal manner or in a distal-to-proximal manner includes advancing a stent delivery system to a target location in a body lumen. The stent delivery lumen includes an inner member having a distal tip and a stent support member disposed over or surrounds the inner member. The stent support member has a stent receiving region proximal of the distal tip of the inner member. A stent surrounds the stent receiving region of the stent support member. The system also includes an outer sleeve having a proximal portion and a distal portion located distal of the proximal portion. The distal portion surrounds the stent to retain the stent in a collapsed configuration. The method further includes deploying the stent in a proximal-to-distal manner or in a distal-to proximal manner. The stent is deployed in the proximal-to distal manner by rotating the inner member relative to the proximal portion of the outer sheath in a first rotational direction to selectively decouple distal portion of the outer sheath from the proximal portion of the outer sheath, and then moving the distal portion of the outer sheath distally relative to the stent to uncover the stent. The stent is deployed in the distal-to-proximal manner by rotating the inner member relative to the proximal portion of the outer sheath in a second rotational direction, opposite the first rotational direction, to selectively decouple distal portion of the outer sheath from the distal tip, and then moving the distal portion of the outer sheath proximal relative to the stent to uncover the stent.

Alternatively or additionally, in another example, the stent delivery system includes a proximal junction detachably coupling the distal portion of the outer sheath to the proximal portion of the outer sheath and a distal junction detachably coupling the distal end of the outer sheath to the distal tip of the inner member.

The above summary of some embodiments is not intended to describe each disclosed embodiment or every implementation of the present disclosure. The Figures, and Detailed Description, which follow, more particularly exemplify some of these embodiments.

BRIEF DESCRIPTION OF THE DRAWINGS

In the drawings, which are not necessarily drawn to scale, like numerals may describe similar components in different views. The drawings illustrate generally, by way of example, but not by way of limitation, various embodiments discussed in the present document.

FIG. 5A is a side view of first and second stents deployed in a body lumen, with the distal stent overlapping the proximal stent;

FIG. 5B is a side view of first and second stents deployed in a body lumen, with the proximal stent overlapping the distal stent;

FIGS. 7A and 7B are cross-sectional views of a body lumen with a stricture and a stent placed asymmetrically across the stricture;

FIG. 7C is a cross-sectional view of a body lumen with a stricture and a stent placed symmetrically across the stricture;

FIG. 8A is a perspective view of a stent delivery device in accordance with another embodiment of the disclosure;

FIG. 8B is a perspective view of the stent delivery device of FIG. 8A deploying a stent in a midsection-first manner;

FIG. 9A is a cross-sectional view of a body lumen with a stricture;

FIG. 9D is a cross-sectional view of the body lumen of FIG. 9C with the stent fully deployed;

FIG. 10A is a perspective view of a stent delivery device in accordance with another embodiment of the disclosure;

FIG. 10B is a perspective view of the stent delivery device of FIG. 10A with the stent partially deployed;

FIG. 11A is a perspective view of a stent delivery device in accordance with another embodiment of the disclosure;

FIG. 11B is a perspective view of the stent delivery device of FIG. 11A with the stent partially deployed;

FIG. 12A is a perspective view of a stent delivery device in accordance with another embodiment of the disclosure;

FIG. 12B is a perspective view of the stent delivery device of FIG. 12A with the stent partially deployed;

Figure 1:
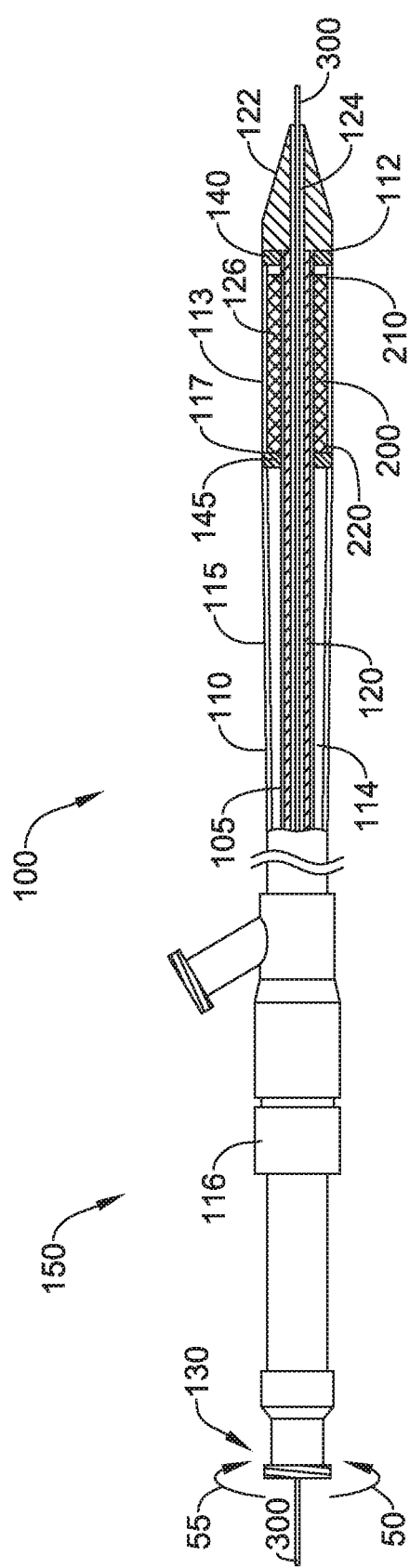
FIG. 1 is a side view of a stent delivery system in accordance with an embodiment of the disclosure, including a cross-sectional view of the distal portion thereof.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification. Definitions of certain terms are provided below and shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure. The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications may be disclosed, one of skill in the art, incited by the present disclosure, would understand desired dimensions, ranges and/or values may deviate from those expressly disclosed.

As used in this specification and the appended claims, the singular forms "a," "an," and "the" include or otherwise refer to singular as well as plural referents, unless the content clearly dictates otherwise. As used in this specification and the appended claims, the term "or" is generally employed to include "and/or," unless the content clearly dictates otherwise.

It is noted that references in the specification to "an embodiment", "an example", "some embodiments", "some examples", "another embodiment", "another example" etc., indicate that the embodiment or example described may include one or more particular features, structures, and/or characteristics. However, such recitations do not necessarily mean that all embodiments or examples include the particular features, structures, and/or characteristics. Additionally, when particular features, structures, and/or characteristics are described in connection with one embodiment or example, it should be understood that such features, structures, and/or characteristics may also be used connection with other embodiments and examples whether or not explicitly described unless clearly stated to the contrary.

The following detailed description should be read with reference to the drawings in which similar elements in different drawings are numbered the same. The detailed description and the drawings, which are not necessarily to scale, depict illustrative embodiments and are not intended to limit the scope of the disclosure. The illustrative embodiments depicted are intended only as exemplary. Selected features of any illustrative embodiment may be incorporated into an additional embodiment unless clearly stated to the contrary.

FIG. 1 illustrates a stent delivery device 100 that includes an outer sheath 110, a stent support 105, and an inner member 120 extending through and longitudinally slidable within the stent support 105 and the outer sheath 110. The outer sheath 110 may cover the majority of the device 100 excluding a portion of the distal end of the device 100. The outer sheath 110 may be characterized by a flexible tube which includes one or more lumens 114.

The inner member 120 may extend through the lumen 114 of the outer sheath 110. Guidance elements such as pull wires (not shown) may be disposed with the lumen 114, or one or more additional lumens to help navigate the delivery device 100 and/or actuate one or more components of the delivery device 100. The device 100 may be sized and configured for use in a range of medical applications, including, but not limited to, vascular applications or gastrointestinal applications, such as biliary, esophageal or colonic applications.

The inner member 120 may include a distal tip 122 at the distal end thereof, and a handle 130 or other component of a handle assembly 150 at a proximal end thereof. The inner member 120 may include a tubular portion extending between the handle 130 and the distal tip 122, with the tubular portion extending through the lumen 114 of the outer sheath 110 and through the stent support 105. The inner member 120 may include at least one lumen 124 extending therethrough. For example, the lumen 124 may extend from the handle 130 to the distal tip 122 through the tubular portion, or along any portion of inner member 120. In some instances, the stent delivery device 100 may be routed over a guidewire 300, which may be received through the lumen 124.

The stent support 105 may be positioned in the lumen 114 of the outer sheath 110. For example, the stent support 105 may extend from a distal end adjacent the distal end 112 of the outer sheath 110 to a proximal end disposed within the handle assembly 150, as illustrated in FIG. 1. The inner member 120 may slidably extend through a lumen of the stent support 105. The stent support 105 may be fixed to the handle assembly 150 such that the stent support 105 remains stationary when axially moving the outer sheath 110 and the inner member 120. In other words, the outer sheath 110 may be longitudinally actuated relative to the stent support 105 and the inner member 120 may be longitudinally actuated relative to the stent support 105. The stent support 105 may include at least one stent receiving region 126 located along a distal region of the stent support 105, such as disposed proximal of the distal tip 122. A stent 200 may be disposed over or surround the stent support 105 in the stent receiving region 126, such that the stent 200 may surround the stent support 105 and the inner member 120 extending therethrough. The stent 200 may be a self-expanding stent, configured to automatically expand to an expanded state from a constrained state when deployed from the stent delivery device 100. The stent 200 may be made from self-expanding or shape memory alloys such as nitinol, spring steels, resilient polymer, or other materials known in the art for making self-expanding stents. The stent 200 may have one or more markers (not shown) such as radiopaque markers, disposed on the distal end 210, proximal end 220, or both ends. When markers are present on both the distal and proximal ends 220, 210 of the stent 200, the markers may be the same or different. Additionally, alignment markers (not shown) may be disposed on the outer sheath 110 and/or the inner member 120 to show rotational orientation and/or torqueing of the elements relative to each other. The alignment markers may be radiopaque and may be placed at any location along the length of the device, as desired.

The outer sheath 110 may extend from a distal end 112, which may be located adjacent to and/or abut the distal tip 122, to a proximal end connected to a handle assembly 150, such as a handle and/or a sliding member 116. The outer sheath 110 may be slidable relative to the inner member 120, the stent support 105 and stent 200 to uncover the stent 200. For example, the distal portion 113 of the outer sheath 110 surrounding the stent 200 may be moveable relative to the stent 200, the stent support 105 and inner member 120 in a proximal direction (e.g., the distal portion 113 of the outer sheath 110 may be moveable in a proximal direction while holding the stent support 105 and inner member 120 stationary relative to the patient) to release the stent 200 in a distal-to-proximal manner, and the distal portion 113 of the outer sheath 110 may be moveable relative to the stent 200, the stent support 105 and the proximal portion 115 of the outer sheath 110 in a distal direction (e.g., the distal portion 113 of the outer sheath 110 may be moveable in a distal direction while holding the stent support 105 and proximal portion 115 of the outer sheath 110 stationary relative to the patient) to release the stent 200 in a proximal-to-distal manner, as will be described in more detail below. The distal portion 113 of the outer sheath 110 surrounding the stent 200, may hold the self-expanding stent 200 in its reduced diameter delivery configuration until unconstrained by the outer sheath 110.

Figure 4:
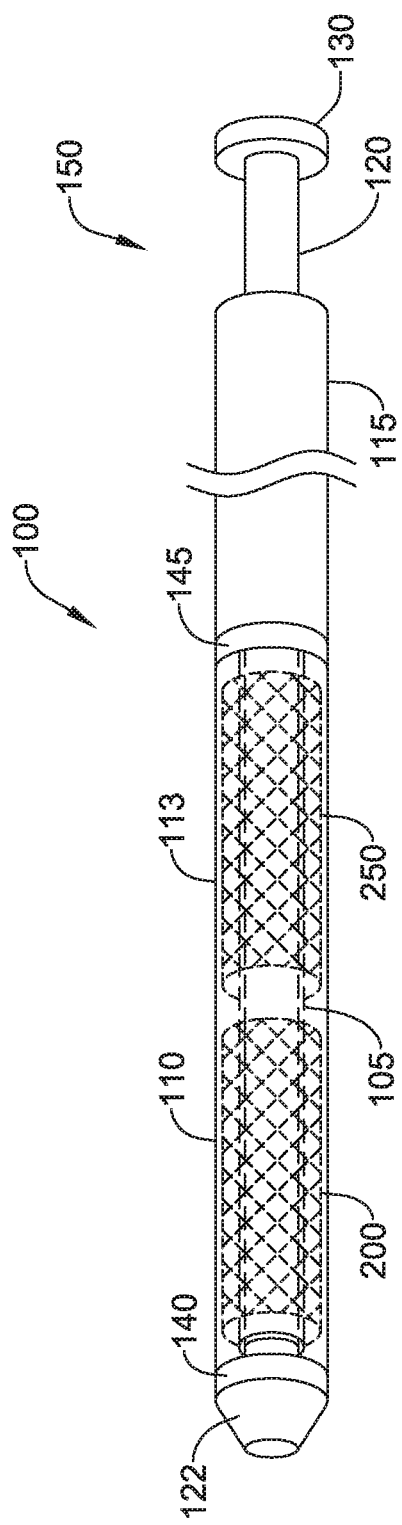
FIG. 4 is a partial cross-sectional view of a stent delivery system including two separate stents.

The handle assembly 150, such as the handle 130 connected to the inner member 120 and the sliding member 116 connected to the proximal end of the outer sheath 110 may allow a physician to move the inner member 120 and the outer sheath 110 longitudinally relative to each other and/or relative to the stent support 105, resulting in the distal portion 113 of the outer sheath 110 translating in either a proximal or distal direction relative to the stent 200, thus releasing the stent 200 in the targeted area of the body lumen as the stent 200 is uncovered by the distal portion 113 of the outer sheath 110. The distal portion 113 of the retractable outer sheath 110 may be flexible or rigid, and is generally used to retain the stent 200 in a constrained, reduced diameter configuration, and protect the wall of the body lumen. The distal portion 113 of the outer sheath 110 may be formed of a material which provides tensile strength, but is flexible, and may in some instances include a reinforcement structure such as a braid, coil, a super elastic alloy, polymer, stainless steel or other similar composites. In some embodiments, the distal portion 113 of the outer sheath 110 may have a length that is at least as long as or longer than the stent 200 such that the distal end 112 of the distal portion 113 of the outer sheath 110 is located distal of the distal end of the stent 200 while the proximal end 117 of the distal portion 113 of the outer sheath 110 is located proximal of the proximal end of the stent 200 in the delivery configuration. In some examples, the length of the stent receiving region 126 of the stent support 105 and/or the distal portion 113 may be more than twice the length of the stent 200, allowing two stents to be deployed with the device 100. The two stents may be disposed over the stent receiving region 126 of the stent support 105 in an end-to-end, spaced-apart configuration, as illustrated in FIG. 4. For example, a first stent 200 may be positioned distal of a second stent 250.

Two separate junctions allow for the distal portion 113 of the outer sheath 110 to be moved in either a proximal or distal direction relative to the stent 200, thereby releasing either the distal or proximal end of the stent 200 first, respectively. A distal junction 140 releasably couples the distal tip 122 of the inner member 120 to the distal end 112 of the distal portion 113 of the outer sheath 110, and a proximal junction 145 releasably couples the proximal end 117 of the distal portion 113 of the outer sheath 110 to the distal end of the proximal portion 115 of the outer sheath 110.

The distal junction 140 may be located proximate to the distal end of the stent 200 and the proximal junction 145 may be located proximate to the proximal end of the stent 200. For example the distal junction 140 may be located distal of the distal end of the stent 200, while the proximal junction 145 may be located proximal of the proximal end of the stent 200.

The distal and proximal junctions 140, 145 may have a number of connection mechanisms, including for example, friction fits, snap fits, keyed connections, rotational connections, barbed connections, threaded connections, bayonet connections, frangible connections, as well as other connections known in the art. In some instances, the junction 140/145 may have a breakable, tearable, frangible, or separatable region. The separatable region may be perforated or have a thinned region of the wall of the outer sheath 110 such that a proximal pulling force on the proximal portion 115 of the outer sheath 110 while distally advancing the inner member 120 and thereby the distal portion 113, causes the separatable region to tear, break, or otherwise separate. Alternatively or additionally, torsional rotational force on the proximal portion 115 of the outer sheath 110 relative to the distal portion 113 of the outer sheath 110 may cause the separatable region to tear, break, or otherwise separate. The distal and proximal junctions 140, 145 may have the same or different connection mechanisms.

In one example, the distal junction 140 may have a two part connection mechanism, such as interlocking male and female parts in a keyed or threaded connection, that is released by twisting or rotating the male and female parts relative to each other. One of the male and female parts may be secured to or otherwise provided with the inner member 120 (e.g., the distal tip 122 of the inner member 120) and the other of the male and female parts may be secured to or otherwise provided with the outer sheath 110 (e.g., at the distal end of the distal portion 113). In another example, the distal junction 140 may involve three or more parts. In one example, the distal junction 140 may be disconnected or released by rotating the inner member 120 relative to the distal portion 113 of the outer sheath 110. For example, the inner member 120 may be rotated in a clockwise direction by rotating the handle 130 clockwise (see arrow 50). The clockwise rotation of the inner member 120 may move the male and female parts relative to each other, thereby releasing the keyed connection and uncoupling the distal end 112 of the distal portion 113 of the outer sheath 110 from the distal tip 122 of the inner member 120. In another example, the handle 130 may alternatively be rotated counter-clockwise to release the distal junction 140, and thus uncouple the distal end 112 of the distal portion 113 of the outer sheath 110 from the distal tip 122 of the inner member 120.

The proximal junction 145 may involve mating parts on the outer sheath 110 between the proximal portion 115 and the distal portion 113. In one example, the proximal junction 145 may include male and female parts interlocking in a keyed connection. One of the male and female parts may be secured to or otherwise provide with the proximal end 117 of the distal portion 113 of the outer sheath 110 and the other of the male and female parts may be secured to or otherwise provided with the distal end of the proximal portion 115. In another example, one of the male and female parts may be secured to or otherwise provided with the distal portion 113 or proximal portion 115 of the outer sheath 110 and the other of the male and female parts may be secured to or otherwise provided with the inner member 120. In a further example, the proximal junction 145 may include three or more components, such as at least one on each of the distal and proximal portions 113, 115 of the outer sheath 110 and at least one on the inner member 120.

In one example, the proximal junction 145 may involve a connection mechanism, such as a threaded connection, between the proximal end 117 of the distal portion 113 and the distal end of the proximal portion 115 of the outer sheath 110. The proximal junction 145 may be disconnected or released by rotating the inner member 120 relative to the proximal portion 115 of the outer sheath 110. For example, the inner member 120 may be rotated in a counter-clockwise direction by rotating the handle 130 counter-clockwise (see arrow 55). The counter-clockwise rotation of the inner member 120 may move the male and female parts relative to each other, thereby releasing the keyed connection and uncoupling the distal portion 113 of the outer sheath 110 from the proximal portion 115 of the outer sheath 110. In another example, the handle 130 may alternatively be rotated clockwise to release the proximal junction 145, and thus uncouple the proximal end 117 of the distal portion 113 of the outer sheath 110 form the distal end of the proximal portion 115 of the outer sheath 110.

It is noted that the direction of rotational movement of the inner member 120 to uncouple the distal junction 140 may be opposite the direction of rotational movement of the inner member 120 to uncouple the proximal junction 145. For instance, in one embodiment clockwise rotation of the inner member 120 may uncouple the distal junction 140 while the proximal junction 145 may remain secured coupled. Likewise, counter-clockwise rotation of the inner member 120 may uncouple the proximal junction 145 while the distal junction 140 may remain securely coupled. Alternatively, in another embodiment counter-clockwise rotation of the inner member 120 may uncouple the distal junction 140 while the proximal junction 145 may remain secured coupled. Likewise, clockwise rotation of the inner member 120 may uncouple the proximal junction 145 while the distal junction 140 may remain securely coupled.

The rotational motions required for releasing the distal and proximal junctions 140, 145 are different (e.g., opposite), allowing the user to have complete control over which junction is uncoupled for deployment of the stent 200. In the above example, the distal junction 140 is released by a clockwise rotation of the handle 130 and the proximal junction 145 is released by a counter-clockwise rotation of the handle 130, however, the configuration may be reversed, if desired.

The amount of rotation required for releasing the distal junction 140 may be any desired amount. For example, the required amount of rotation for uncoupling the distal junction 140 may be from 45 to 180 degrees or 45 degrees to 120 degrees in some instances. For example, in some instances the required amount of rotation for uncoupling the distal junction 140 may be about 45 degrees or more, about 90 degrees or more, about 120 degrees or more, about 150 degrees or more, or 180 degrees or more. In other instances the required amount of rotation for uncoupling the distal junction 140 may be about 45 degrees or less, about 90 degrees or less, about 120 degrees or less, about 150 degrees or less, or 180 degrees or less.

The amount of rotation required for releasing the proximal junction 145 may be any desired amount. For example, the required amount of rotation for uncoupling the proximal junction 145 may be from 45 to 180 degrees or 45 degrees to 120 degrees in some instances. For example, in some instances the required amount of rotation for uncoupling the proximal junction 145 may be about 45 degrees or more, about 90 degrees or more, about 120 degrees or more, about 150 degrees or more, or 180 degrees or more. In other instances the required amount of rotation for uncoupling the proximal junction 145 may be about 45 degrees or less, about 90 degrees or less, about 120 degrees or less, about 150 degrees or less, or 180 degrees or less.

When rotation of the inner member 120 relative to the proximal portion 115 of the outer sheath 110 provides the necessary motion to release the distal and proximal junctions 140, 145, the release positions for the distal junction 140 and the proximal junction 145 may be 180 degrees apart, for example. For instance, the device 100 may be provided in a start or rest position, characterized as a delivery configuration (the position in which the elements of the device are disposed relative to one another when the device is inserted into the body) such that rotation of the handle 130 from the rest position to 90 degrees in a first rotational direction (e.g., clockwise) uncouples the distal junction 140 while the proximal junction 145 remains coupled, and rotation of the handle from the rest position 90 degrees in a second rotational direction (e.g., counter-clockwise) uncouples the proximal junction 145 while the distal junction 140 remains coupled.

Figure 6:
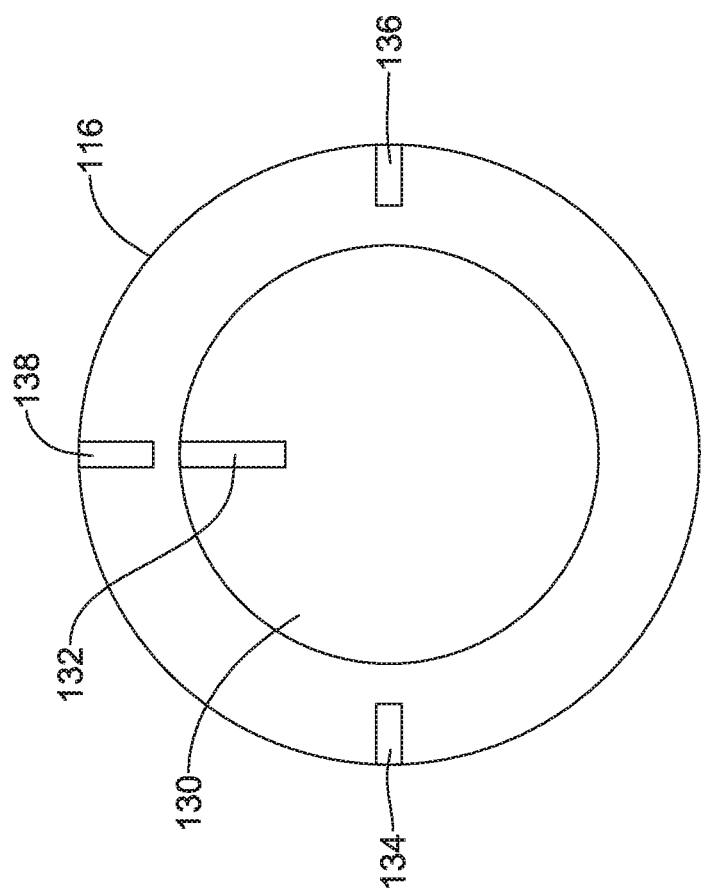
FIG. 6 is a proximal end view of a handle and outer sheath assembly of an exemplary stent delivery device.

FIG. 6 illustrates markings that may be present on the handle assembly 150, such as the handle 130 and sliding member 116 that provide a visual indication of the rotational orientation of the inner member relative to the proximal portion 115 of the outer sheath 110. For example, the handle 130 may have a position marker 132 and the sliding member 116 may have three location marks: a start or rest position marker 138, a first rotational marker 136 arranged in a clockwise rotation from the start or rest position marker 138, and a second rotational marker 134 arranged in a counter-clockwise rotation from the start or rest position marker 138. The markers may aid the physician in determining how far to rotate the handle 130 relative to the sliding member 116 (and thus how far to rotate the inner member 120 relative to the proximal portion 115 of the outer sheath 110) in order to selectively uncouple the distal junction 140 or the proximal junction 145. The clockwise rotational marker 136 and/or the counter-clockwise rotational marker 134 may be placed at an desired rotational positions, such as the 90 degree offset from the rest position marker 138 as illustrated in FIG. 6. However, the rotational position markers 134, 136 may be placed at another desired rotational position. For example, the markers 134, 136 may be positioned at any position between 45 and 180 degrees away from the rest position marker 138. In some instances, the clockwise and counter-clockwise rotational markers 136, 134 may include a letter or word label, or other visual indicia, indicating which junction of the proximal and distal junctions is uncoupled when rotated to the indicated position. For example, if the distal junction is uncoupled by rotation of the handle 130 (and thus the inner member 120) in a clockwise direction, the clockwise rotation mark 136 may include the letter "D" or the word "Distal". Similarly, if the proximal junction is uncoupled by rotation the handle 130 (and thus the inner member 120) in a counter-clockwise direction, the counter-clockwise rotation mark 134 may include the letter "P" or the word "Proximal". It will be understood that the directions may be reversed, with a clockwise rotation of the handle 130 uncoupling the proximal junction and a counter-clockwise rotation of the handle 130 uncoupling the distal junction.

In some embodiments, such as shown in FIG. 4, the stent delivery system may be configured to deliver multiple stents. A device containing two stents will allow one stent to be released in a distal-to-proximal manner and the other stent to be released in a proximal-to-distal manner. For example, from the rest position, the handle 130 may be rotated 90 degrees clockwise to uncouple the distal junction 140 and deploy the distal stent 200 in a distal-to-proximal manner. The handle 130 may then be rotated 90 degrees counter-clockwise back to the rest position (which may recouple the distal junction in some instances) and then further rotated 90 degrees counter-clockwise to uncouple the proximal junction 145 to deploy the proximal stent 250. The rotational actions may be reversed, with the 90 degree counter-clockwise rotation from the rest position performed first to release the second stent in the proximal-to-distal manner, followed by the 180 degree clockwise rotation to release the first stent in the distal-to-proximal manner. It is noted that the order of deploying the stents may be reversed, in which the proximal junction may be uncoupled first to deploy the proximal stent 250, followed by decoupling the distal junction to deploy the distal stent 200.

To prepare the stent delivery device 100 the stent 200 may be compressed and loaded onto the stent receiving region 126 and covered by the distal portion 113 of the outer sheath 110 to constrain the stent 200 in a collapsed configuration for delivery. The inner member 120 or the stent support 105 may include stopping elements (not shown) disposed proximal of and distal to the stent, or underneath a proximal portion and/or distal portion of the stent 200. The proximal stopping element may prevent proximal movement of the stent 200, and the distal stopping element may prevent distal movement of the stent 200 when the distal portion 113 of the outer sheath 110 is retracted proximally or advanced distally to release the stent 200. The proximal and distal stopping elements may be in the form of a protrusion, a ring, a band, a stepped increase in outer diameter, a bushing, a sleeve, or any other structure that prevents proximal or distal movement of the stent 200.

The distal portion 113 of the outer sheath 110 may surround or cover the underlying stent 200 during the advancement of the stent 200 by the delivery device to a desired target location within a body lumen of the patient. During the placement of the stent 200, the distal portion 113 of the outer sheath 110 may protect the stent 200 from contact with an intimal surface of the body lumen.

The proximal portion of the stent delivery device 100, as shown in FIG. 1, may include a handle assembly 150 configured to selectively retract the distal portion 113 of the outer sheath 110 proximally relative to the stent 200 after decoupling the distal junction 140. For example, the handle assembly 150 may include a sliding member 116 connected to the outer sheath 110 and slidably integrated between the distal and proximal ends of the handle assembly 150. By retracting the sliding member 116 in a distal to proximal longitudinal direction, the distal portion 113 of outer sheath 110 may be retracted proximally relative to the stent 200 and stent support 105, exposing the stent 200 in a distal-to-proximal manner. The handle assembly 150 may also be configured to selectively advance the distal portion 113 of the outer sheath 110 distally relative to the stent 200 after decoupling the proximal junction 145. For example, the handle assembly 150 may include a handle 130 connected to the inner member 120. By advancing the handle 130 in a proximal to distal longitudinal direction, the distal portion 113 of the outer sheath 110 may be advanced distally relative to the stent 200 and stent support 105, exposing the stent 200 in a proximal-to-distal manner. It is noted that the handle assembly 150 may include other actuation means for selectively moving the distal portion 113 of the outer sheath 110 in either a proximal or distal direction relative to the stent 200.

Figure 2:
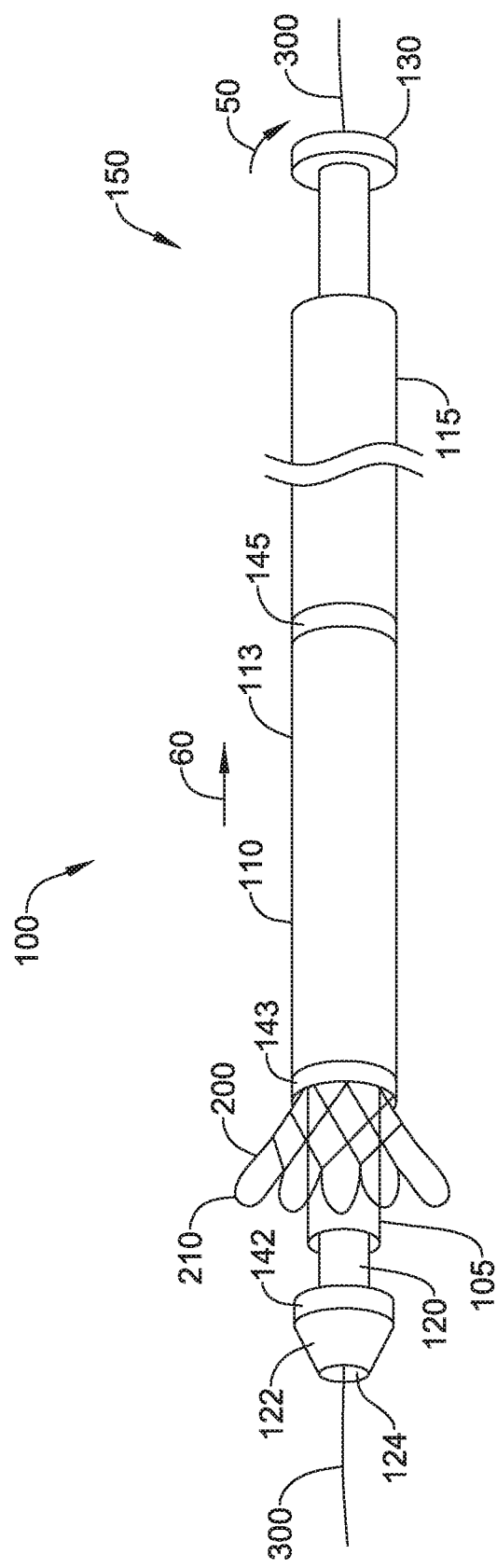
FIG. 2 is a perspective view of a stent delivery device deploying a stent in a distal-to-proximal manner.
Figure 3:
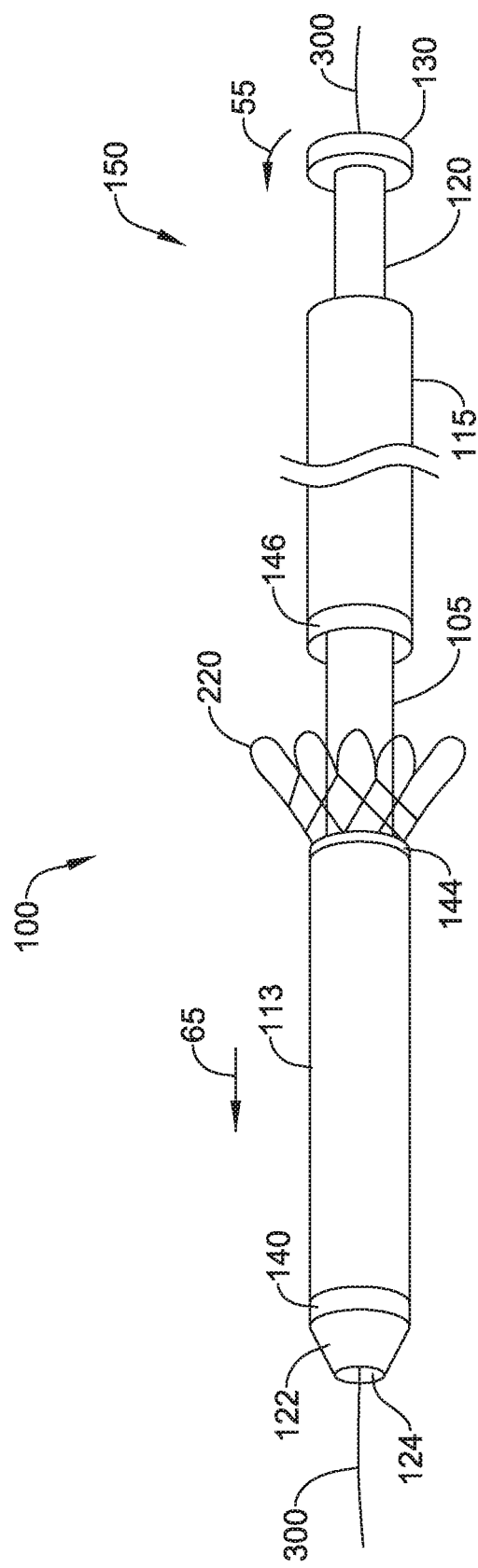
FIG. 3 is a perspective view of a stent delivery device deploying a stent in a proximal-to-distal manner.

The two different deployment modes are illustrated in FIGS. 2 and 3. FIG. 2 illustrates uncoupling of the distal junction 140, allowing a distal-to-proximal deployment of the stent 200. When the outer sheath 110 is in its distal-most position, the distal portion 113 covers the stent 200 and the distal end 112 is connected to the distal tip 122 at the distal junction 140. When the distal junction 140 is uncoupled, the outer sheath 110 may be moved proximally, and/or the inner member 120 and stent support 105 may be moved distally (and thus the stent 200), separating the distal end 112 from the distal tip 122 at the distal junction 140, exposing the distal end 210 of the stent 200. As the stent 200 is exposed, the exposed distal portion of the stent 200, now unconstrained by the distal portion 113 of the outer sheath 110, will automatically expand radially outward towards its expanded configuration. Further proximal movement of the outer sheath 110 or distal movement of the inner member 120 exposes the entire stent 200, allowing the stent 200 to expand in a distal-to-proximal manner.

In the example illustrated in FIG. 2, the distal junction 140 is a two part connection, with a first distal junction element 142 attached to, or otherwise provided with the distal tip 122 of the inner member 120, and a second distal junction element 143 attached to, or otherwise provided with the distal end of the distal portion 113 of the outer sheath 110. Distal junction elements 142 and 143 may be rotatably connected. As the inner member 120 is rotated in a first rotational direction relative to the proximal portion 115 of the outer sheath 110, distal junction elements 142 and 143 rotate relative to each other and disengage from one another.

A force F, indicated by arrow 60, may be applied to the outer sheath 110 in a proximal direction, retracting the distal portion 113 of the outer sheath 110 from the stent 200. The force F may be applied to the sliding member 116, for example. As the outer sheath 110 is pulled proximally, thus moving the distal portion 113 proximally relative to the stent 200, the distal end 210 of the stent 200 is exposed and begins to expand, as illustrated in FIG. 2. The proximal junction 145 remains coupled with the proximal portion 115 of the outer sheath 110 coupled to the distal portion 113 of the outer sheath 110. Thus, the stent 200 may be deployed gradually in a distal-to-proximal manner.

In some situations it may be more beneficial to deploy the stent 200 in a proximal-to-distal manner, especially when the location of placement of the proximal end 220 of the stent 200 is more important than placement of the distal end 210 of the stent 200. For example, stenting the colon/rectal junction where strictures are present. Placement of the stent 200 in a location too far proximal may result in rectal dysfunction and placement too far distal may lead to incomplete stricture resolution and stent migration.

FIG. 3 illustrates the uncoupling of the proximal junction 145, allowing a proximal-to-distal deployment of the stent 200. The proximal junction 145 may be a two part connection, with a first proximal junction element 144 attached to, or otherwise provided with the proximal end of the distal portion 113 of the outer sheath 110, and a second proximal junction element 146 attached to, or otherwise provided with the distal end of the proximal portion 115 of the outer sheath 110. Proximal junction elements 144 and 146 may be rotatably connected. As the inner member 120 is rotated in a second rotational direction (opposite the first rotational direction) relative to the proximal portion 115 of the outer sheath 110, proximal junction elements 144 and 146 rotate relative to each other and disengage from one another. A force F, indicated by arrow 65, may be applied to the inner member 120 in a distal direction, advancing the inner member 120 along with the distal portion 113 of the outer sheath 110, coupled to the distal tip 122, distally off the stent 200. The force F may be applied to the inner member 120 by pushing the handle 130, for example. As the inner member 120 is pushed distally, thus moving the distal portion 113 distally relative to the stent 200, the proximal end 220 of the stent 200 is exposed and begins to expand, as illustrated in FIG. 3. The distal junction 140 remains coupled with the distal portion 113 of the outer sheath 110 coupled to the distal tip 122 of the inner member 120. Thus, the stent 200 may be deployed gradually in a proximal-to-distal manner.

In other examples, one of the proximal junction elements 144, 146 may be disposed on the inner member 120. Alternatively the proximal junction 145 may include one or more additional elements that may be disposed on the inner member 120, and may interact with the proximal junction elements 144, 146 to disengage the distal portion 113 of the outer sheath 110 from the proximal portion 115.

The device 100 may include a locking mechanism (not shown) that prevents the handle 130 from being rotated until the distal region is in position at the desired location within the body lumen and the stent 200 is to be deployed. Such a locking mechanism will prevent the unintentional deployment of the stent 200. The locking mechanism may be a lever, tab, pin, or any other conventional structure used to prevent rotation of one element relative to another element.

The ability to selectively deploy a stent either in a distal-to-proximal or a proximal-to-distal manner with a single device provides the advantage of allowing the physician to make the decision regarding deployment direction at the time of deployment, and requires minimal additional training over conventional distal-to-proximal deployment devices. Additionally, because the device 100 may be operated to release either the distal or proximal junction, two stents may be delivered using the device, with one stent deployed in a distal-to-proximal manner and another stent deployed in a proximal-to-distal manner.

FIG. 4 illustrates a distal stent 200 and a proximal stent 250 disposed within the device 100. The distal stent 200 may be disposed over or surround the stent support 105 and the inner member 120 extending therethrough near the distal tip 122. The proximal stent 250 may be disposed proximal of the distal stent 200. Both stents 200, 250 may be disposed between the distal junction 140 and the proximal junction 145. The device 100 may be actuated as discussed above, in a first example, with both stents being deployed in the distal-to-proximal manner by uncoupling the distal junction 140 and withdrawing the outer sheath 110, including the distal portion 113, proximally over the distal stent 200 and then the proximal stent 250 to sequentially expose the distal stent 200 and then the proximal stent 250. In a second example, both stents may be deployed in the proximal-to-distal manner by uncoupling the proximal junction 145 and advancing the distal portion 113 of the outer sheath 110 distally over the proximal stent 250 and then the distal stent 200 to sequentially expose the proximal stent 250 and then the distal stent 200. In a third example, the distal stent 200 may be deployed in the distal-to-proximal manner by uncoupling the distal junction 140 and withdrawing the outer sheath 110, including the distal portion 113, proximally over the distal stent 200 to expose the distal stent 200, followed by deploying the proximal stent 250 in the proximal-to-distal manner by uncoupling the proximal junction 145 and advancing the distal portion 113 of the outer sheath 110 distally over the proximal stent 250 to expose the proximal stent 250. The distal junction 140 may be recoupled prior to deploying the proximal stent 250. In a fourth example, the proximal stent 250 may be deployed in the proximal-to-distal manner followed by deploying the distal stent 200 in the distal-to-proximal manner. In such an instances, the proximal junction 145 may be recoupled prior to deploying the distal stent 200.

The two stents may be deployed at spaced apart locations or in an overlapping configuration within a body lumen 5, as illustrated in FIGS. 5A and 5B. Either of the stents 200, 250 may be deployed first, in either a distal-to-proximal or proximal-to-distal manner, allowing the stents to overlap in either of two configurations. In the examples shown in FIGS. 5A and 5B, stent 200 is used as the first stent, however it will be understood that either the distal or proximal stent as provided in the device 100 may be deployed first. In FIG. 5A, the stent 200 is deployed first and allowed to expand. Once the first stent 200 has expanded, the device 100 may be positioned with the distal end of the remaining stent 250 positioned inside the proximal end of the first stent 200, and then the second stent 250 may be deployed in a distal-to-proximal manner, which allows for precise positioning of the distal end of the second stent 250 inside the first stent 200, with an overlap region 240.

FIG. 5B illustrates the opposite orientation of the two stents. As in the above example, stent 200 is deployed first and allowed to expand. The first stent may be deployed in either the distal-to-proximal or proximal-to-distal manner. Once the first stent 200 has expanded, the device 100 is positioned with the proximal end of the second stent 250 positioned inside the distal end of the first stent, and the second stent 250 is deployed in a proximal-to-distal manner, which allows for precise positioning of the proximal end of the second stent 250 inside the first stent 200, with an overlap region 240.

Current self-expanding stents as exemplified by those used in endoscopic applications are often delivered via a delivery system that incorporates a stent retaining outer sheath which when retracted allows the stent to expand at the required target site within the body lumen. This delivery method allows the stent to deploy in a gradual manner from distal to proximal at the designated stricture site. However, due to stent foreshortening, body lumen tortuosity or other reasons in some instances delivery at the stricture site it may prove difficult to center the stent over the stricture as desired. As illustrated in FIGS. 7A and 7B, this may lead to the stent 200 being positioned non-symmetrically over the stricture 8 in the body lumen 5, which may lead to stent migration or inefficient stricture resolution. This may be especially prevalent in the case of trainee physicians with less experience in device placement. The desired position of the stent 200 is illustrated in FIG. 7C, placed symmetrically over the stricture 8 in the body lumen 5.

The stent delivery device 500 illustrated in FIGS. 8A and 8B offers the ability to deploy a stent 200 centered on the stricture irrespective of foreshortening or other design considerations with minimal additional training. The stent delivery device 500 may include an outer sheath 510 and an inner member 520 extending through and longitudinally slidable within the outer sheath 510. The inner member 520 may extend through the lumen of the outer sheath 510 as well as through the stent 200. Guidance elements such as pull wires (not shown) may be disposed with the lumen, or one or more additional lumens to help navigate the delivery device 500 and/or actuate one or more components of the delivery device 500. The device 500 may be sized and configured for use in a range of medical applications, including, but not limited to, vascular applications or gastrointestinal applications, such as biliary, esophageal or colonic applications.

The inner member 520 may include a distal tip 522 at the distal end thereof, and a handle 530 at a proximal end thereof. The inner member 520 may include at least one lumen 524 extending therethrough. For example, the lumen 524 may extend from the handle 530 to the distal tip 522 through the tubular portion, or along any portion of inner member 520. In some instances, the stent delivery device 500 may be routed over a guidewire 300, which may be received through the lumen 524.

The stent 200 may be a self-expanding stent, configured to automatically expand to an expanded state from a constrained state when deployed from the stent delivery device 500. The stent 200 may be made from self-expanding or shape memory alloys such as nitinol, spring steels, resilient polymer, or other materials known in the art for making self-expanding stents. The stent 200 may have one or more markers (not shown) such as radiopaque markers, disposed on the distal end, proximal end, midsection 230 or all three regions. When markers are present on both the distal and proximal ends and midsection 230 of the stent 200, the markers may be the same or different. Additionally, alignment markers (not shown) may be disposed on the outer sheath 510 and/or the inner member 520 to show rotational orientation and/or torqueing of the elements relative to each other. The alignment markers may be radiopaque and may be placed at any location along the length of the device, as desired.

The outer sheath 510 may extend from the distal tip 522 to a proximal end connected to a handle assembly (not shown). The distal portion 513 of the outer sheath 510 may be fixed to the distal tip 522. A middle junction 560 may be located between the distal portion 513 and the proximal portion 515 of the outer sheath 510. The middle junction 560 may be disposed over the midsection 230 of the stent 200. The middle junction 560 may have any one of a number of connection mechanisms, including for example, friction fits, snap fits, keyed connections, rotational connections, barbed connections, threaded connections, bayonet connections, frangible connections, as well as other connections known in the art. In one example, the middle junction 560 may have a two part connection mechanism, such as interlocking male and female parts in a keyed or threaded connection, that is released by twisting or rotating the male and female parts relative to each other. One of the male and female parts may be secured to or otherwise provided with the distal portion 513 of the outer sheath 510 and the other of the male and female parts may be secured to or otherwise provided with the proximal portion 515 of the outer sheath 510. The inner member 520, distal tip 522, and distal portion 513 of the outer sheath 510 may all be fixed together. Clockwise or counter-clockwise rotation of the inner member 520 via handle 530 may move the male and female parts of the middle junction 560 relative to each other, thereby releasing the connection and uncoupling the distal portion 513 of the outer sheath 510 from the proximal portion 515 of the outer sheath 510.

In some instances, the middle junction 560 may have a breakable, tearable, frangible, or separatable region 562. The separatable region 562 may be perforated or have a thinned region of the wall of the outer sheath 510 such that a proximal pulling force on the proximal portion 515 of the outer sheath 510 while distally advancing the inner member 520 and thereby the distal portion 513, causes the separatable region 562 to tear, break, or otherwise separate. Alternatively or additionally, torsional rotational force on the proximal portion 515 of the outer sheath 510 relative to the distal portion 513 of the outer sheath 510 may cause the separatable region 562 to tear, break, or otherwise separate. Once the middle junction 560 has been separated, the proximal portion 515 and the distal portion 513 of the outer sheath 510 are moved in opposite directions. This may be achieved by applying a distal force as indicated by arrow 512 to the distal portion 513 of the outer sheath 510 through advancement of the inner member 520 distally, and/or by applying a proximal force as indicated by arrow 514 to the proximal portion 515 of the outer sheath 510.

Figure 9B:
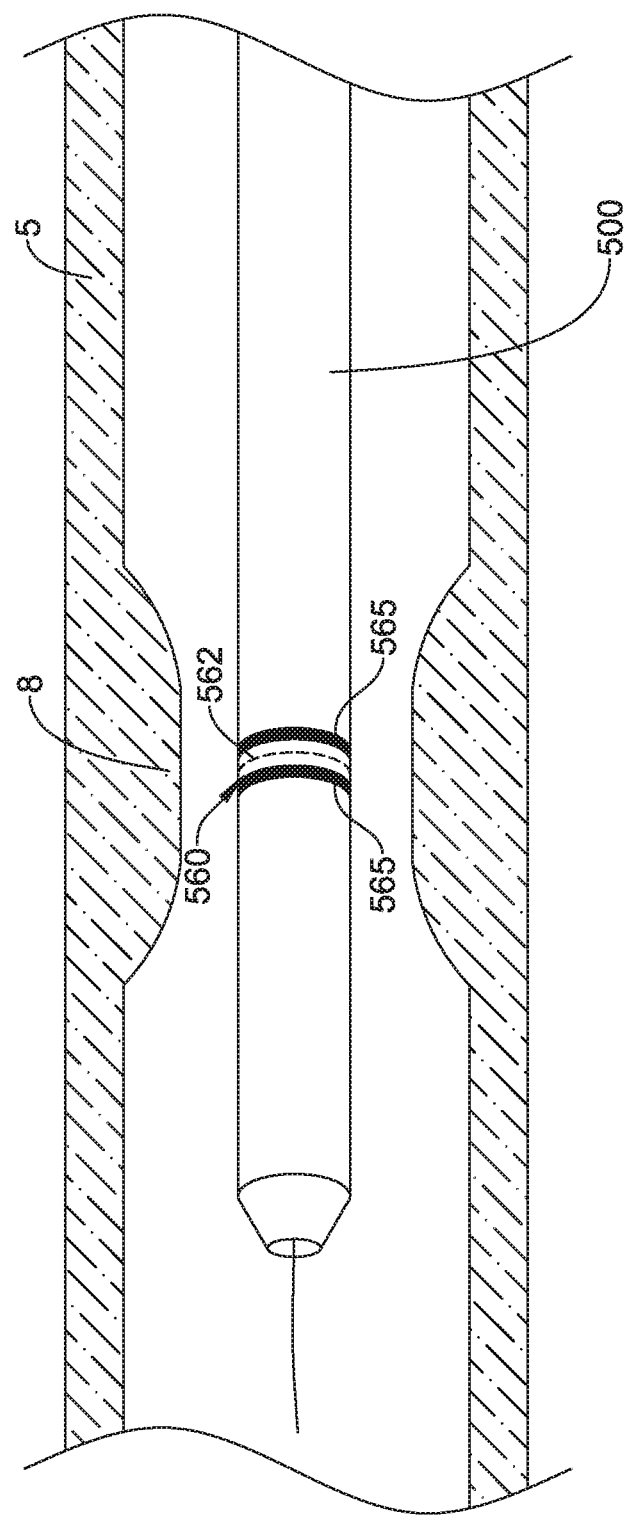
FIG. 9B is a cross-sectional view of the body lumen of FIG. 9A with a stent delivery device in perspective view.
Figure 9C:
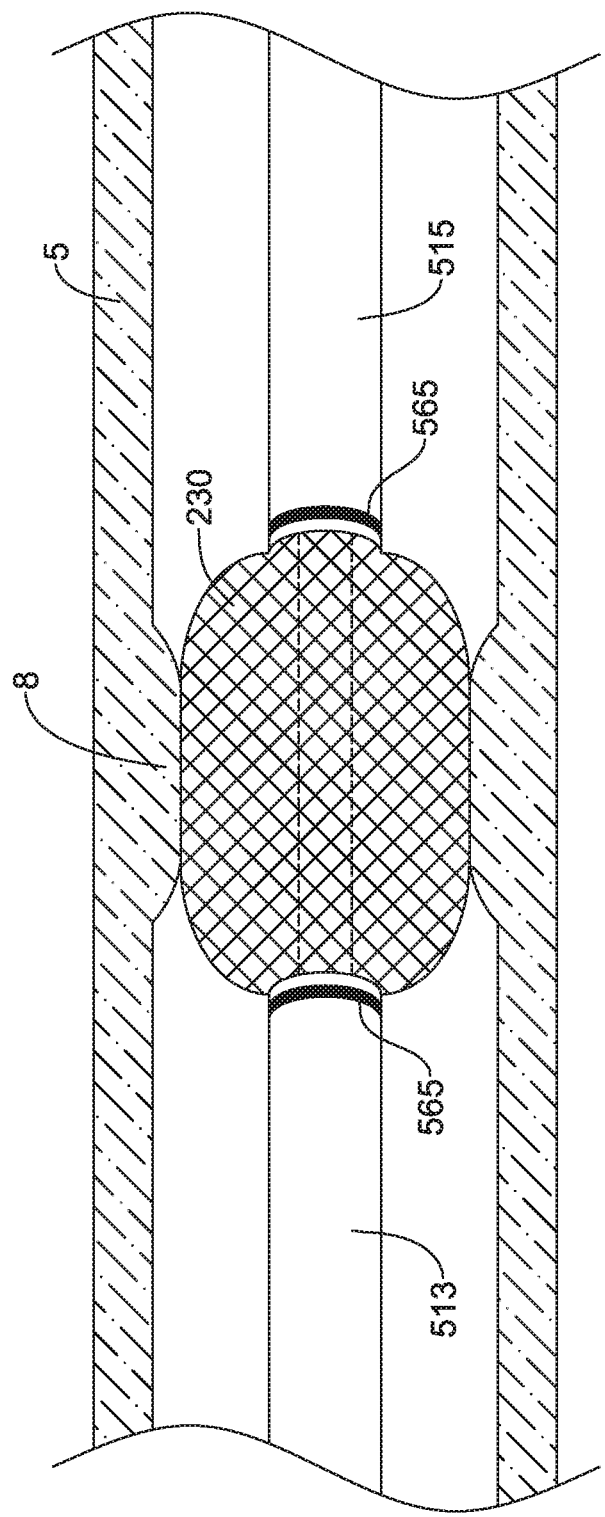
FIG. 9C is a cross-sectional view of the body lumen of FIG. 9B with the stent partially deployed in a midsection-first manner.

FIGS. 9A-9D illustrate the deployment of a stent 200 using the stent delivery device 500. FIG. 9A shows the stricture 8 in the body lumen 5. In FIG. 9B, the delivery device 500 is positioned with the middle junction 560 centered within the stricture 8. In some instance, the stent delivery device 500 may include one or more radiopaque markers 565 configured to facilitate centering the middle junction 560 within the stricture 8. For example, the middle junction 560 may include a first radiopaque marker 565 located just proximal of the separatable region 562 on the proximal portion 515 of the outer sheath 510 and a second radiopaque marker 565 located just distal of the separatable region 562 on the distal portion 513 of the outer sheath 510. The stent midsection 230 is disposed under the middle junction 560, thus the stent 200 is positioned centered within the stricture 8. The stent midsection 230 is uncovered, as shown in FIG. 9C, and the stent 200 expands from the midsection 230 towards the distal and proximal ends. Expanding the midsection 230 of the stent first allows the midsection to be precisely placed over the stricture, anchoring the stent 200. Any foreshortening of the stent 200 happens on both distal and proximal stent ends at the same time, and the anchoring of the midsection 230 prevents axial movement of the stent 200 relative to the stricture 8. The stent 200 is delivered centered over the stricture 8, as shown in FIG. 9D.

One drawback of a sheathed stent may be the overall length of the delivery device that must be tracked to release the stent. It may be advantageous if the stent could be released with less tracking being performed. Two embodiments that may allow the stent to be released proximal-to-distal or distal-to-proximal and reduce the amount of delivery system that needs to be tracked to deliver the stent are shown in FIGS. 10A, 10B, 11A, and 11B.

FIG. 10A shows a stent delivery device 600 with a distal portion 613 of the outer sheath 610 having three sections 625, 630, 635. The distal portion 613 of the outer sheath 610 may have a distal axially collapsible section 625, such as a distal braided section, a solid middle section 630, and a proximal axially collapsible section 635, such as a proximal braided section. The overall structure of the stent delivery device 600 is the same as the delivery device 100 shown in FIGS. 2 and 3, with two separate junctions allowing for either a proximal-to-distal or distal-to-proximal release of the stent 200. The delivery device 600 has a distal junction 640 that releasably couples the distal tip 622 of the inner member 620 to the distal end of the distal axially collapsible section 625 of the distal portion 613, and a proximal junction 645 that releasably couples the proximal end of the proximal axially collapsible section 635 to the distal end of the proximal portion 615 of the outer sheath 610. The distal axially collapsible section 625 and the proximal axially collapsible section 635 have ends which form the locking junctions 640, 645 and may be braided, include a helical spring, corrugated, axially elongated, or made from a memory type material (metallic or polymeric). These axially collapsible sections 625, 635, which are axially stretched or elongated under tension when the junctions 640, 645 are coupled during delivery, are formed to contract in length to a shortened longitudinal length or profile when not under tension, such as once one or more of the junctions 640, 645 are uncoupled or separated. For example, the length of the distal portion 613 of the outer sheath 610 (i.e., the combined length of the distal axial collapsible section 625, the solid middle section 630, and the proximal axial collapsible section 635), e.g., the distance from the proximal junction 645 to the distal junction 640, may be a length $L_1$ when the junctions 640, 645 are coupled and the distal and proximal axially collapsible sections 625, 635 are axially elongated under tension with the distal axially collapsible section 625 having an elongated length $L_2$ and the proximal axially collapsible section 635 having an elongated length $L_3$. Once one of the junctions 640, 645 is uncoupled or separated, the length of the distal portion 613 of the outer sheath 610 (i.e., the combined length of the distal axial collapsible section 625, the solid middle section 630, and the proximal axial collapsible section 635), e.g., the distance from the proximal junction 645 to the distal junction 640, may be a length $L_4$, less than the initial length $L_1$. For example, when the distal junction 640 is uncoupled or separated, the distal axially collapsible section 625 and/or the proximal axially collapsible section 635 may be axially collapsed to a shorter length, with the distal axially collapsible section 625 having an axially collapsed length $L_5$ less than $L_2$ and/or the proximal axially collapsible section 635 having an axially collapsed length $L_6$ less than $L_3$. Similarly, when the proximal junction 645 is uncoupled or separated, the proximal axially collapsible section 635 and/or the distally axially collapsible section 625 may be axially collapsed to a shorter length, with the proximal axially collapsible section 635 having an axially collapsed length $L_6$ less than $L_3$ and/or the distal axially collapsible section 625 having an axially collapsed length $L_5$ less than $L_2$. It is noted that the proximal axially collapsible section 635 and/or the distal axially collapsible section 625 may also be radially contracted, (i.e., have a smaller inner diameter) when axially stretched in tension to closely contact the outer surface of the stent 200. The solid middle section 630 may be a standard solid portion such as the proximal portion 615 of the outer sheath 610, as shown in FIG. 10A. The solid middle section 630, which may maintain a constant length, may not change in length when the distal and/or proximal junction 640, 645 is coupled or separated. The stent 200 may be expanded against an inner surface of the solid middle section 630 such that the solid middle section 630 does not move axially proximally or distally when the proximal junction 645 or distal junction 640 is uncoupled or separated.

When the proximal junction 645 or the distal junction 640 is separated or uncoupled through torqueing (rotation) of the inner member 620 and/or outer sheath 610, the axially collapsible sections 625, 635 revert or return back to an axially shortened profile (e.g., may return to or toward an equilibrium configuration), releasing the stent end (e.g., the distal end of the distal axially collapsible section 625 moves toward the middle section 630 and/or the proximal end of the proximal axially collapsible section 635 moves toward the middle section 630). The solid middle section 630 ensures that some portion of the stent is retained and not fully released to aid in more accurate placement. Advancement of the inner member 620 distally and/or advancement of the proximal portion 615 proximally can then fully release the stent 200. However, axial displacement of the inner member 620 and/or the proximal portion 615 of the outer sheath 610 may be less than that needed to fully deploy the stent 200 if the entire length of the distal portion 613 were to remain constant after decoupling the junction 640/645.

In a similar manner another stent delivery device 700 may have an outer sheath 710 with a distal axially collapsible section 725, such as a distal corrugated section, a solid middle section 730, and a proximal axially collapsible section 735, such as a proximal corrugated section. The corrugated sections 725, 735 may be configured with a tendency to be retracted in a controllable fashion or elasticated to spring back to or toward a reduced axial length equilibrium configuration, as shown in FIGS. 11A and 11B.

The overall structure of the stent delivery device 700 may be the same as the delivery device 100 shown in FIGS. 2, 3, and 10A-10B, with two separate junctions allowing for either a proximal-to-distal or distal-to-proximal release of the stent 200. The delivery device 700 has a distal junction 740 that releasably couples the distal tip 722 of the inner member 720 to the distal end of the distal axially collapsible section 725 of the distal portion 713, and a proximal junction 745 that releasably couples the proximal end of the proximal axially collapsible section 735 to the distal end of the proximal portion 715 of the outer sheath 710.

To maintain rigidity in the undeployed configuration, the corrugations in the corrugated sections 725, 735 on the outer sheath 710 may interface with corrugations 775 on a saddle or stent support 770 that carries the stent 200 and interfaces with the inner member 720. Torqueing or rotation of the inner member 720 and/or the outer sheath 710 may cause the proximal junction 745 or distal junction 740 to separate and the stent support corrugations 775 to separate from the outer sheath 710 corrugations, allowing the outer sheath 710 to retract, as in FIG. 11B.

These axially collapsible sections 725, 735, which are axially stretched or elongated under tension when the junctions 740, 745 are coupled during delivery, are formed to contract in length to a shortened longitudinal length or profile when not under tension, such as once one or more of the junctions 740, 745 are uncoupled or separated. For example, the length of the distal portion 713 of the outer sheath 710 (i.e., the combined length of the distal axial collapsible section 725, the solid middle section 730, and the proximal axial collapsible section 735), e.g., the distance from the proximal junction 745 to the distal junction 740, may be a length $L_1$ when the junctions 740, 745 are coupled and the distal and proximal axially collapsible sections 725, 735 are axially elongated under tension with the distal axially collapsible section 725 having an elongated length $L_2$ and the proximal axially collapsible section 735 having an elongated length $L_3$. Once one of the junctions 740, 745 is uncoupled or separated, the length of the distal portion 713 of the outer sheath 710 (i.e., the combined length of the distal axial collapsible section 725, the solid middle section 730, and the proximal axial collapsible section 735), e.g., the distance from the proximal junction 745 to the distal junction 740, may be a length $L_4$, less than the initial length $L_1$. For example, when the distal junction 740 is uncoupled or separated, the distal axially collapsible section 725 and/or the proximal axially collapsible section 735 may be axially collapsed to a shorter length, with the distal axially collapsible section 725 having an axially collapsed length $L_5$ less than $L_2$ and/or the proximal axially collapsible section 735 having an axially collapsed length $L_6$ less than $L_3$. Similarly, when the proximal junction 745 is uncoupled or separated, the proximal axially collapsible section 735 and/or the distally axially collapsible section 725 may be axially collapsed to a shorter length, with the proximal axially collapsible section 735 having an axially collapsed length $L_6$ less than $L_3$ and/or the distal axially collapsible section 725 having an axially collapsed length $L_5$ less than $L_2$. It is noted that the proximal axially collapsible section 735 and/or the distal axially collapsible section 725 may also be radially contracted, (i.e., have a smaller inner diameter) when axially stretched in tension to closely contact the outer surface of the stent 200. The solid middle section 730 may be a standard solid portion such as the proximal portion 715 of the outer sheath 710, as shown in FIG. 11A. The solid middle section 730, which may maintain a constant length, may not change in length when the distal and/or proximal junction 740, 745 is coupled or separated. The stent 200 may be expanded against an inner surface of the solid middle section 730 such that the solid middle section 730 does not move axially proximally or distally when the proximal junction 745 or distal junction 740 is uncoupled or separated.

In a similar manner another stent delivery device 800 may have an outer sheath 810 with a distal axially collapsible section 825, which may include a helical spring 860, a solid middle section 80, and a proximal axially collapsible section 835, which may include a helical spring. The sections 825, 835 may be configured with a tendency to be spring back to or toward a reduced axial length equilibrium configuration, as shown in FIGS. 12A and 12B.

The overall structure of the stent delivery device 800 may be the same as the delivery device 100 shown in FIGS. 2, 3, and 10A-10B, with two separate junctions allowing for either a proximal-to-distal or distal-to-proximal release of the stent 200. The delivery device 800 has a distal junction 840 that releasably couples the distal tip 822 of the inner member 820 to the distal end of the distal axially collapsible section 825 of the distal portion 813, and a proximal junction 845 that releasably couples the proximal end of the proximal axially collapsible section 835 to the distal end of the proximal portion 815 of the outer sheath 810.

These axially collapsible sections 825, 835, in which the helical springs 860 may be axially stretched or elongated under tension when the junctions 840, 845 are coupled during delivery, are formed to contract in length to a shortened longitudinal length or profile when not under tension, such as once one or more of the junctions 840, 845 are uncoupled or separated. For example, the length of the distal portion 813 of the outer sheath 810 (i.e., the combined length of the distal axial collapsible section 825, the solid middle section 830, and the proximal axial collapsible section 835), e.g., the distance from the proximal junction 845 to the distal junction 840, may be a length $L_1$ when the junctions 840, 845 are coupled and the distal and proximal axially collapsible sections 825, 835 are axially elongated under tension with the distal axially collapsible section 825 having an elongated length $L_2$ and the proximal axially collapsible section 835 having an elongated length $L_3$. Once one of the junctions 840, 845 is uncoupled or separated, the length of the distal portion 813 of the outer sheath 810 (i.e., the combined length of the distal axial collapsible section 825, the solid middle section 830, and the proximal axial collapsible section 835), e.g., the distance from the proximal junction 845 to the distal junction 840, may be a length $L_4$, less than the initial length $L_1$. For example, when the distal junction 840 is uncoupled or separated, the distal axially collapsible section 825 and/or the proximal axially collapsible section 835 may be axially collapsed to a shorter length (e.g., through axial contraction of the spring(s) 860), with the distal axially collapsible section 825 having an axially collapsed length $L_5$ less than $L_2$ and/or the proximal axially collapsible section 835 having an axially collapsed length $L_6$ less than $L_3$. Similarly, when the proximal junction 845 is uncoupled or separated, the proximal axially collapsible section 835 and/or the distally axially collapsible section 825 may be axially collapsed to a shorter length (e.g., through axial contraction of the spring(s) 860), with the proximal axially collapsible section 835 having an axially collapsed length $L_6$ less than $L_3$ and/or the distal axially collapsible section 825 having an axially collapsed length $L_5$ less than $L_2$. It is noted that the proximal axially collapsible section 835 and/or the distal axially collapsible section 825, including the springs 860, may also be radially contracted, (i.e., have a smaller inner diameter) when axially stretched in tension to closely contact the outer surface of the stent 200. The solid middle section 830 may be a standard solid portion such as the proximal portion 815 of the outer sheath 810, as shown in FIG. 12A. The solid middle section 830, which may maintain a constant length, may not change in length when the distal and/or proximal junction 840, 845 is coupled or separated. The stent 200 may be expanded against an inner surface of the solid middle section 830 such that the solid middle section 830 does not move axially proximally or distally when the proximal junction 845 or distal junction 840 is uncoupled or separated.

Figure 13A:
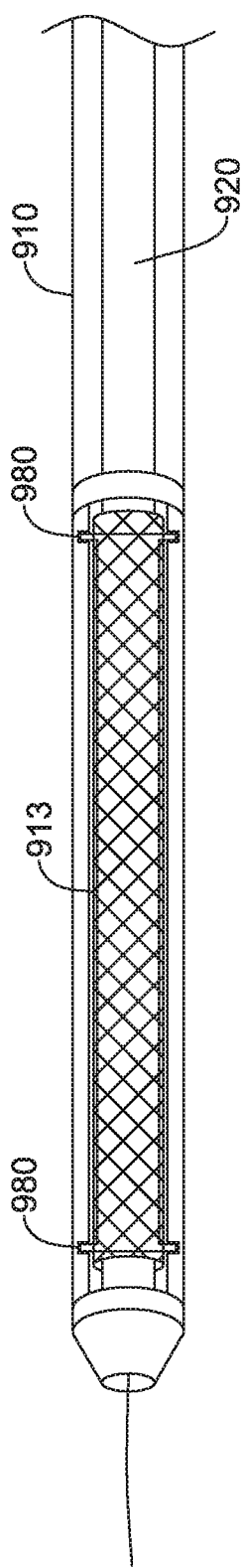
FIG. 13A is a perspective view of a stent delivery device in accordance with another embodiment of the disclosure.
Figure 13B:
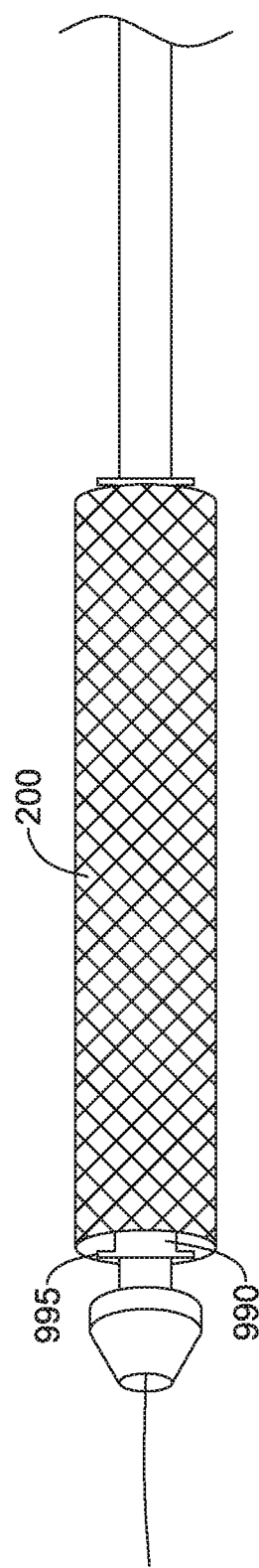
FIG. 13B is a perspective view of the stent delivery device of FIG. 13A with the outer sheath removed.

For all of the embodiments described above that have distal and proximal junctions for releasing the stent in either a distal-to-proximal or proximal-to-distal manner, an alternative locking mechanism may be provided. As shown in FIGS. 13A and 13B, the outer sheath 910 may have a plurality of notches 980 on the inner surface in various places radially around the circumference at the proximal and distal end of the distal portion 913. These notches 980 may interface with raised pins 995 disposed at various places radially around the circumference of the stent support 990 that carries the stent 200 and interfaces with the inner member 920. Torqueing or rotating of the inner member 920 causes the pins 995 at the proximal or distal end of the stent support 990 and the notches 980 in the outer sheath 910 to unlock and allow the stent 200 to expand, as in FIG. 13B.

The materials that can be used for the various components of the delivery device 100 (and/or other devices disclosed herein) and the various tubular members disclosed herein may include those commonly associated with medical devices. For simplicity purposes, the following discussion makes reference to outer sheath 110 and inner member 120 and other components of device 100. However, this is not intended to limit the devices and methods described herein, as the discussion may be applied to other similar devices and/or components of devices or devices disclosed herein.

The various components of the devices/systems disclosed herein may include a metal, metal alloy, polymer (some examples of which are disclosed below), a metal-polymer composite, ceramics, combinations thereof, and the like, or other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro (propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

In at least some embodiments, portions or all of the delivery device 100 and/or other components of delivery system may be doped with, made of, or otherwise include a radiopaque material. Radiopaque materials are understood to be materials capable of producing a relatively bright image on a fluoroscopy screen or another imaging technique during a medical procedure. This relatively bright image aids the user of the delivery device 100 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the delivery device 100 to achieve the same result.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:
1. A stent delivery system comprising:
   an elongated inner member extending between a distal tip and a proximal end;
   a stent support member disposed over the inner member and defining a stent receiving region, the inner member slidable within the stent support member;
   at least one stent surrounding the stent receiving region of the stent support member, the stent having a collapsed configuration and an expanded configuration;
   an elongated outer sheath slidably disposed over the inner member, the outer sheath extending between a distal end and a proximal end, the outer sheath including a proximal portion and a distal portion located distal of the proximal portion, the distal portion of the outer sheath surrounding the stent to restrain the stent in the collapsed configuration;
   a proximal junction detachably coupling the distal portion of the outer sheath to the proximal portion of the outer sheath, the proximal junction being actuatable to selectively uncouple the distal portion of the outer sheath from the proximal portion of the outer sheath;
   a distal junction detachably coupling the distal end of the outer sheath to the distal tip of the inner member, the distal junction being actuatable to selectively uncouple the outer sheath from the distal tip;
   wherein the distal and proximal junctions are separately actuatable by rotating the inner member relative to the proximal portion of the outer sheath with the proximal portion of the outer sheath held stationary; and a handle assembly at the proximal end of the inner member, wherein the handle assembly includes a position marker and first and second spaced apart rotational markers indicating a rotational orientation of the inner member;

wherein the proximal junction is uncoupled when the position marker is aligned with the first rotational marker, and wherein the distal junction is uncoupled when the position marker is aligned with the second rotational marker.

2. The stent delivery system of claim 1, wherein the distal junction includes a first distal junction element disposed on the distal tip and a second distal junction element disposed on the distal end of the outer sheath, wherein the first and second distal junction elements are rotatably coupled to each other.

3. The stent delivery system of claim 1, wherein the proximal junction includes a first proximal junction element disposed on a proximal end of the distal portion of the outer sheath, a second proximal junction element disposed on a distal end of the proximal portion of the outer sheath, wherein the first and second proximal junction elements are rotatably coupled to each other.

4. The stent delivery system of claim 1, wherein the stent is deployable from a proximal-to-distal manner by uncoupling the proximal junction and moving the distal portion of the outer sleeve distally relative to the stent.

5. The stent delivery system of claim 1, wherein the stent is deployable from a distal-to-proximal manner by uncoupling the distal junction and moving the distal portion of the outer sleeve proximally relative to the stent.

6. The stent delivery system of claim 1, further comprising start position marker located between the first rotational marker and the second rotational marker, wherein both the proximal junction and the distal junction are coupled when the position marker is aligned with the start position marker.

7. The stent delivery system of claim 6, wherein the first and second rotational markers are arranged 180 degrees apart.

8. The stent delivery system of claim 1, wherein a length of the distal portion of the outer sheath is at least as long as a length of the stent.

9. The stent delivery system of claim 1, wherein the proximal junction is adjacent a proximal end of the stent.

10. The stent delivery system of claim 1, wherein the distal and proximal junctions include one or more of a threaded connection, a bayonet connection, a snap fit connection, a keyed connection, a rotational connection, and a barbed connection.

11. The stent delivery system of claim 1, wherein the distal portion of the outer sheath includes at least one axially collapsible section configured to shorten in axial length when the proximal junction or the distal junction is uncoupled.

12. A stent delivery system comprising:
an elongated inner member extending between a distal tip and a proximal end;
a stent support member disposed over the inner member and defining a stent receiving region, the inner member slidable within the stent support member;
at least one stent surrounding the stent receiving region of the stent support member, the stent having a collapsed configuration and an expanded configuration;
an elongated outer sheath slidably disposed over the inner member, the outer sheath extending between a distal end and a proximal end, the outer sheath including a proximal portion and a distal portion located distal of the proximal portion, the distal portion of the outer sheath surrounding the stent to restrain the stent in the collapsed configuration;
a proximal junction detachably coupling the distal portion of the outer sheath to the proximal portion of the outer sheath, the proximal junction being actuatable to selectively uncouple the distal portion of the outer sheath from the proximal portion of the outer sheath; and
a distal junction detachably coupling the distal end of the outer sheath to the distal tip of the inner member, the distal junction being actuatable to selectively uncouple the outer sheath from the distal tip;
wherein the distal and proximal junctions are separately actuatable by rotating the inner member relative to the proximal portion of the outer sheath with the proximal portion of the outer sheath held stationary;
wherein the distal portion of the outer sheath includes at least one axially collapsible section configured to shorten in axial length when the proximal junction or the distal junction is uncoupled;
wherein the at least one axially collapsible section includes a proximal axially collapsible section and a distal axially collapsible section; and
wherein the distal portion includes a middle section positioned between the proximal and distal axially collapsible sections, the middle section configured to maintain a constant length when the proximal junction or the distal junction is uncoupled.

13. A stent delivery system comprising:
an elongated inner member having a proximal end and a distal end, the inner member including a distal tip at the distal end;
a stent support member disposed over the inner member and having a stent receiving region proximal of the distal tip of the inner member, the inner member being slidably disposed within the stent support member;
at least one self-expanding stent disposed over the stent receiving region of the stent support member, the stent having a collapsed configuration and an expanded configuration;
an elongated outer sheath slidably disposed over the inner member, the outer sheath extending between a distal end and a proximal end, the outer sheath including a proximal portion and a distal portion located distal of the proximal portion, the distal portion of the outer sheath extending to the distal end of the outer sheath and surrounding the stent to restrain the stent in the collapsed configuration;
a proximal junction detachably coupling a proximal end of the distal portion of the outer sheath to a distal end of the proximal portion of the outer sheath, the proximal junction being actuatable to selectively uncouple the distal portion of the outer sheath from the proximal portion of the outer sheath by rotating the inner member relative to the proximal portion of the outer sheath in a first rotational direction with the proximal portion of the outer sheath held stationary; and
a distal junction detachably coupling the distal end of the outer sheath to the distal tip of the inner member, the distal junction being actuatable to selectively uncouple the outer sheath from the distal tip by rotating the inner member relative to the proximal portion of the outer sheath in a second rotational direction with the proximal portion of the outer sheath held stationary;
wherein the first direction is opposite the second direction;

wherein the distal portion of the outer sheath includes at least one axially collapsible section configured to shorten in axial length when the proximal junction or the distal junction is uncoupled;

wherein the at least one axially collapsible section includes a proximal axially collapsible section and a distal axially collapsible section; and wherein the distal portion includes a middle section positioned between the proximal and distal axially collapsible sections, the middle section configured to maintain a constant length when the proximal junction or the distal junction is uncoupled.

14. The stent delivery system of claim 13, wherein the distal junction includes a first distal junction element disposed on the distal tip and a second distal junction element disposed on the distal end of the outer sheath, wherein the first and second distal junction elements are rotatably coupled to each other; and wherein the proximal junction includes a first proximal junction element disposed on the proximal end of the distal portion of the outer sheath, a second proximal junction element disposed on the distal end of the proximal portion of the outer sheath, wherein the first and second proximal junction elements are rotatably coupled to each other.

15. The stent delivery system of claim 14, wherein the distal portion of the outer sheath has a first length when:
 i) the first and second proximal junction elements are rotatably coupled to each other, and
 ii) the first and second distal junction elements are rotatably coupled to each other, wherein the distal portion of the outer sheath has a second length when:
 i) the first and second proximal junction elements are rotatably uncoupled from each other and the first and second distal junction elements are rotatably coupled to each other; or
 ii) the first and second proximal junction elements are rotatably coupled to each other and the first and second distal junction elements are rotatably uncoupled from each other;

wherein the second length is less than the first length.

16. The stent delivery system of claim 13, wherein the proximal axially collapsible section includes a braid and the distal axially collapsible section includes a braid.

* * * * *